United States Patent
Schuele et al.

(10) Patent No.: US 10,736,780 B2
(45) Date of Patent: *Aug. 11, 2020

(54) LASER EYE SURGERY SYSTEM

(71) Applicant: AMO Development, LLC, Santa Ana, CA (US)

(72) Inventors: Georg Schuele, Menlo Park, CA (US); Phillip Gooding, Mountain View, CA (US)

(73) Assignee: AMO Development, LLC, Santa Ana, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/849,314

(22) Filed: Dec. 20, 2017

(65) Prior Publication Data

US 2018/0133058 A1    May 17, 2018

Related U.S. Application Data

(60) Division of application No. 14/575,884, filed on Dec. 18, 2014, now Pat. No. 9,849,033, which is a
(Continued)

(51) Int. Cl.
| | |
|---|---|
| *A61F 9/008* | (2006.01) |
| *A61B 3/10* | (2006.01) |
| *A61B 3/14* | (2006.01) |

(52) U.S. Cl.
CPC ........ *A61F 9/00804* (2013.01); *A61B 3/1025* (2013.01); *A61B 3/14* (2013.01);
(Continued)

(58) Field of Classification Search
None
See application file for complete search history.

(56) References Cited

U.S. PATENT DOCUMENTS

| | | | |
|---|---|---|---|
| 4,436,388 A | 3/1984 | Takahashi et al. | |
| 4,443,075 A | 4/1984 | Crane et al. | |
| (Continued) | | | |

FOREIGN PATENT DOCUMENTS

| | | |
|---|---|---|
| CN | 1035566 A | 9/1989 |
| CN | 1154658 A | 7/1997 |
| (Continued) | | |

OTHER PUBLICATIONS

American Heritage Dictionary of the English Language, Definition of Bearing, 2007.
(Continued)

*Primary Examiner* — Carl H Layno
*Assistant Examiner* — Manolis Pahakis
(74) *Attorney, Agent, or Firm* — Johnson & Johnson Surgical Vision, Inc.

(57) ABSTRACT

A method for laser eye surgery that accommodates patient movement includes: generating a first and a second electromagnetic radiation beam, the second beam configured to modify eye tissue; propagating the first beam to a scanner along a an optical path length that changes in response to eye movement; focusing the first beam to a first focal point within the eye; scanning the first focal point at different locations within the eye; propagating a portion of the first beam reflected from the first focal point location back along the variable optical path to a sensor; generating an intensity signal indicative of the intensity of the portion of the reflected first beam; propagating the second beam to the scanner along the variable optical path; focusing the second beam to a second focal point and scanning the second focal point to create an incision in the cornea of the eye.

15 Claims, 34 Drawing Sheets

Related U.S. Application Data continuation of application No. 14/191,095, filed on Feb. 26, 2014, now Pat. No. 9,849,032.

(60) Provisional application No. 61/780,736, filed on Mar. 13, 2013.

(52) U.S. Cl.
CPC .......... *A61F 9/008* (2013.01); *A61F 9/00802* (2013.01); *A61F 9/00812* (2013.01); *A61F 9/00836* (2013.01); *A61F 2009/00846* (2013.01); *A61F 2009/00855* (2013.01); *A61F 2009/00868* (2013.01); *A61F 2009/00872* (2013.01); *A61F 2009/00889* (2013.01); *A61F 2009/00897* (2013.01)

(56) References Cited

U.S. PATENT DOCUMENTS

| | | |
|---|---|---|
| 4,452,517 A | 6/1984 | Kohayakawa |
| 4,520,816 A | 6/1985 | Schachar et al. |
| 4,744,642 A | 5/1988 | Yoshinaga et al. |
| 4,761,534 A | 8/1988 | Foulkes |
| 4,964,717 A | 10/1990 | Koester |
| 5,094,523 A | 3/1992 | Reznichenko et al. |
| 5,305,759 A | 4/1994 | Kaneko et al. |
| 5,336,215 A | 8/1994 | Hsueh et al. |
| 5,360,424 A * | 11/1994 | Klopotek ............ A61F 9/00802 606/17 |
| 5,364,390 A | 11/1994 | Taboada et al. |
| 5,445,633 A | 8/1995 | Nakamura et al. |
| 5,446,547 A | 8/1995 | Guenther et al. |
| 5,459,325 A | 10/1995 | Hueton et al. |
| 5,501,226 A | 3/1996 | Petersen et al. |
| 5,549,632 A | 8/1996 | Lai |
| 5,586,981 A | 12/1996 | Hu |
| 5,688,262 A | 11/1997 | Abraham |
| 5,720,894 A | 2/1998 | Neev et al. |
| 5,782,822 A | 7/1998 | Telfair et al. |
| 5,870,167 A | 2/1999 | Knopp et al. |
| 5,880,880 A | 3/1999 | Anderson et al. |
| 5,957,915 A | 9/1999 | Trost |
| 5,973,781 A | 10/1999 | Moeller et al. |
| 5,984,916 A | 11/1999 | Lai |
| 6,004,314 A | 12/1999 | Wei et al. |
| 6,019,472 A | 2/2000 | Koester et al. |
| 6,095,648 A | 8/2000 | Birngruber et al. |
| 6,099,522 A | 8/2000 | Knopp et al. |
| 6,271,915 B1 | 8/2001 | Frey et al. |
| 6,454,761 B1 | 9/2002 | Freedman |
| 6,460,997 B1 | 10/2002 | Frey et al. |
| 6,475,138 B1 | 11/2002 | Schechter et al. |
| 6,585,725 B1 | 7/2003 | Mukai |
| 6,942,656 B2 | 9/2005 | Pawlowski et al. |
| 7,036,934 B1 | 5/2006 | Youssefi et al. |
| 7,158,226 B2 | 1/2007 | Gfroerer et al. |
| 7,278,989 B2 | 10/2007 | Vinciguerra et al. |
| 7,364,296 B2 | 4/2008 | Miller et al. |
| 7,621,637 B2 | 11/2009 | Rathjen et al. |
| 7,655,002 B2 | 2/2010 | Myers et al. |
| 7,717,907 B2 | 5/2010 | Ruiz et al. |
| 7,911,670 B2 | 3/2011 | Bec et al. |
| 7,982,879 B2 | 7/2011 | Desjardins et al. |
| 8,262,646 B2 | 9/2012 | Frey et al. |
| 8,350,183 B2 | 1/2013 | Vogel et al. |
| 8,382,745 B2 | 2/2013 | Naranjo-Tackman et al. |
| 8,414,564 B2 | 4/2013 | Goldshleger et al. |
| 9,044,304 B2 | 6/2015 | Raksi et al. |
| 2001/0010003 A1 | 7/2001 | Lai |
| 2002/0007176 A1 | 1/2002 | Campin et al. |
| 2002/0048025 A1 | 4/2002 | Takaoka |
| 2002/0080359 A1 | 6/2002 | Denk et al. |
| 2002/0082466 A1 | 6/2002 | Han |
| 2004/0012666 A1 | 1/2004 | Sasaki |
| 2004/0075879 A1 | 4/2004 | Karin |
| 2004/0081341 A1 | 4/2004 | Cherek et al. |
| 2004/0143246 A1 | 7/2004 | Maeda et al. |
| 2004/0223385 A1 | 11/2004 | Fleming et al. |
| 2004/0243112 A1 * | 12/2004 | Bendett ............... A61F 9/00827 606/5 |
| 2004/0254568 A1 | 12/2004 | Rathjen |
| 2005/0043597 A1 | 2/2005 | Xie |
| 2005/0211872 A1 | 9/2005 | Kawano et al. |
| 2005/0231727 A1 | 10/2005 | Podoleanu et al. |
| 2006/0106371 A1 | 5/2006 | Muhlhoff et al. |
| 2006/0129141 A1 | 6/2006 | Lin |
| 2006/0187462 A1 | 8/2006 | Srinivasan et al. |
| 2006/0217688 A1 | 9/2006 | Lai |
| 2007/0010804 A1 | 1/2007 | Rathjen et al. |
| 2007/0291277 A1 | 12/2007 | Everett et al. |
| 2008/0081950 A1 | 4/2008 | Koenig et al. |
| 2008/0088938 A1 | 4/2008 | Lai |
| 2008/0218691 A1 | 9/2008 | Fercher |
| 2008/0231803 A1 | 9/2008 | Feldon et al. |
| 2008/0243107 A1 | 10/2008 | Muhlhoff et al. |
| 2008/0278687 A1 | 11/2008 | Somani |
| 2009/0067042 A1 | 3/2009 | Tanikawa et al. |
| 2009/0187176 A1 | 7/2009 | Assa et al. |
| 2009/0279052 A1 | 11/2009 | Hauger et al. |
| 2010/0042081 A1 | 2/2010 | Rathjen |
| 2010/0067020 A1 | 3/2010 | Podoleanu et al. |
| 2010/0069894 A1 | 3/2010 | Mrochen et al. |
| 2010/0076417 A1 | 3/2010 | Suckewer et al. |
| 2010/0089884 A1 | 4/2010 | Sercel et al. |
| 2010/0130968 A1 | 5/2010 | Vogler |
| 2010/0165289 A1 | 7/2010 | Nozato et al. |
| 2010/0256614 A1 | 10/2010 | Donitzky et al. |
| 2011/0028958 A1 | 2/2011 | Raksi et al. |
| 2011/0058175 A1 | 3/2011 | Suehira |
| 2011/0134436 A1 | 6/2011 | Podoleanu et al. |
| 2011/0152845 A1 | 6/2011 | Hammer et al. |
| 2011/0172649 A1 | 7/2011 | Schuele |
| 2011/0218523 A1 | 9/2011 | Robl |
| 2011/0234975 A1 | 9/2011 | Hirose |
| 2011/0245814 A1 | 10/2011 | Taboada et al. |
| 2011/0309231 A1 | 12/2011 | Cooper et al. |
| 2011/0310395 A1 | 12/2011 | Tsai et al. |
| 2011/0319873 A1 | 12/2011 | Raksi et al. |
| 2011/0319875 A1 | 12/2011 | Loesel et al. |
| 2012/0140170 A1 | 6/2012 | Hirose et al. |
| 2012/0218515 A1 | 8/2012 | Imamura |
| 2012/0271286 A1 | 10/2012 | Curatu et al. |
| 2012/0283708 A1 | 11/2012 | Raksi et al. |
| 2013/0050649 A1 | 2/2013 | Juhasz et al. |
| 2013/0072917 A1 * | 3/2013 | Kaschke ............ A61F 9/00736 606/6 |
| 2013/0085483 A1 | 4/2013 | Rathjen |
| 2013/0103014 A1 | 4/2013 | Gooding et al. |
| 2013/0120710 A1 | 5/2013 | Buckland et al. |
| 2013/0131653 A1 | 5/2013 | Huang |
| 2013/0132653 A1 | 5/2013 | Post et al. |
| 2013/0169931 A1 | 7/2013 | Lee et al. |
| 2013/0226157 A1 | 8/2013 | Huang |
| 2013/0226160 A1 | 8/2013 | Rathjen |
| 2013/0261612 A1 | 10/2013 | Yokosuka et al. |
| 2013/0310816 A1 | 11/2013 | Rathjen |
| 2014/0046306 A1 | 2/2014 | Huang et al. |
| 2014/0046308 A1 | 2/2014 | Bischoff et al. |
| 2014/0107634 A1 | 4/2014 | Vogler et al. |
| 2014/0121508 A1 | 5/2014 | Latimer et al. |
| 2014/0128821 A1 | 5/2014 | Gooding et al. |
| 2014/0163534 A1 | 6/2014 | Angeley et al. |
| 2014/0180265 A1 | 6/2014 | Huang |
| 2014/0240674 A1 | 8/2014 | Wei et al. |
| 2014/0257259 A1 | 9/2014 | Papastathopoulos et al. |
| 2014/0276671 A1 | 9/2014 | Gooding et al. |
| 2014/0316389 A1 | 10/2014 | Schuele et al. |
| 2015/0116660 A1 | 4/2015 | Matsumoto et al. |
| 2015/0202083 A1 | 7/2015 | Takeda et al. |
| 2016/0040976 A1 | 2/2016 | Berkeley et al. |
| 2016/0081851 A1 | 3/2016 | Huang |
| 2016/0106582 A1 | 4/2016 | Campos et al. |

(56) References Cited

U.S. PATENT DOCUMENTS

2016/0161244 A1 6/2016 Jaillon et al.
2016/0235588 A1 8/2016 Hart et al.
2017/0000647 A1 1/2017 Schuele et al.

FOREIGN PATENT DOCUMENTS

| CN | 1891184 A | 1/2007 |
|---|---|---|
| DE | 10323422 A1 | 4/2004 |
| DE | 102005001249 A1 | 7/2006 |
| EP | 1486185 A1 | 12/2004 |
| JP | H06277248 A | 10/1994 |
| JP | H06291399 A | 10/1994 |
| JP | H11192253 A | 7/1999 |
| JP | 2000060893 A | 2/2000 |
| JP | 2000139996 A | 5/2000 |
| JP | 2000152954 A | 6/2000 |
| JP | 2008149164 A | 7/2008 |
| JP | 2008534993 A | 8/2008 |
| WO | 9308877 A1 | 5/1993 |
| WO | 2008098381 A1 | 8/2008 |
| WO | 2011094758 A2 | 8/2011 |
| WO | 2011147570 A1 | 12/2011 |
| WO | 2012135579 A2 | 10/2012 |
| WO | 2014158615 A1 | 10/2014 |

OTHER PUBLICATIONS

International Search Report and Written Opinion for Application No. PCT/US2014/018693 dated May 26, 2014, 10 pages.
International Search Report and Written Opinion for Application No. PCT/US2014/018752, dated Jun. 13, 2014, 10 pages.
Partial International Search Report for Application No. PCT/US2016/035905, dated Feb. 9, 2017, 7 pages.

* cited by examiner using the second support assembly to support a second reflector configured to reflect the electromagnetic radiation beam to propagate along a portion of the variable optical path so as to be incident on the first reflector - 222 using the sensor to generate the intensity signal comprises passing a reflected portion of the electromagnetic radiation beam through an aperture to block portions of the electromagnetic radiation beam reflected from locations other than the focal point location - 224

*FIG. 6* passing the electromagnetic radiation beam through a polarization-sensitive device - 226 modifying polarization of at least one of the electromagnetic radiation beam and a portion of the electromagnetic radiation beam reflected from the focal point location - 228 using the polarization-sensitive device to reflect a portion of the electromagnetic radiation beam reflected from the focal point location so as to be incident upon the sensor - 230

*FIG. 7*

| Patterns | Description |
|---|---|
|  | Lens Segmentation: Quadrants (2 intersecting lines) |
|  | Lens Segmentation: Sextants (3 intersecting lines) |
|  | Lens Segmentation: Octants (4 intersecting lines) |
|  | Lens Softening: Quadrants |
|  | Lens Softening: Sextants |
|  | Lens Softening: Octants |
|  | Quadrants Complete |
*FIG. 45*

LASER EYE SURGERY SYSTEM

CROSS-REFERENCES TO RELATED APPLICATIONS

This application claims priority to, and is a divisional of U.S. patent application Ser. No. 14/575,884, filed on Dec. 18, 2014, issued as U.S. Pat. No. 9,849,033, which is a continuation of U.S. patent application Ser. No. 14/191,095, filed Feb. 26, 2014, issued as U.S. Pat. No. 9,849,032, which claims priority to U.S. provisional application No. 61/780,736 filed on Mar. 13, 2013, the entire contents of which are incorporated herein by reference.

FIELD OF THE INVENTION

Laser eye surgery systems have become ubiquitous and varied in purpose. For example, a laser eye surgery system may be configured to reshape the anterior surface of the cornea via ablation to effect a refractive correction. A laser eye surgery system may also be configured to create a corneal flap to expose an underlying portion of the cornea such that the underlying portion can be reshaped via ablation and then recovered with the flap. More recently developed laser eye surgery systems may be configured to create one or more incisions in the cornea or limbus to reshape the cornea, create one or more incisions in the cornea to provide access for a cataract surgery instrument and/or to provide access for implantation of an intraocular lens, incise a capsulotomy in the anterior lens capsule to provide access for removal of a cataractous lens, segment a cataractous lens, and/or incise a capsulotomy in the posterior lens capsule.

Many laser eye surgery systems generate a series of laser beam pulses via a laser beam source. The laser beam pulses propagate along an optical path to the patient's eye. The optical path typically includes controllable elements such as scanning mechanisms and/or focusing mechanisms to control the direction and/or location of the emitted laser beam pulses relative to the patient.

Some laser eye surgery systems are configured to track eye movement (e.g., change of viewing direction of the eye) such that control over the direction and/or location of the emitted laser beam pulses can be accomplished so as to account for the eye movement. For example, a laser eye surgery system may optically track a feature in the eye, such as a natural feature or a fiduciary marker added to the eye, so as to track movement of the eye.

In contrast, other laser eye surgery systems may be configured to inhibit eye movement. For example, a contact lens may be employed that directly contacts the anterior surface of the cornea so as to restrain eye movement. Such restraint, however, may cause associated patient discomfort and/or anxiety.

Beyond eye movement, many laser eye surgery systems are configured to inhibit relative movement between the patient and the laser eye surgery system. For example, a laser eye surgery system may include some sort of substantial patient restraint feature such as a dedicated support assembly (e.g., chair or bed), which can include restraint features configured to inhibit movement of the patient relative to the support assembly. Such a dedicated support assembly may include a positioning mechanism by which the patient can be moved to position the patient's eye relative to the optical path of the laser eye surgery system. Additionally, a laser eye surgery system may be configured to rigidly support components that determine the location of the optical path of the laser pulses so as to substantially prevent movement of the optical path relative to the dedicated support assembly, thereby also inhibiting relative movement of the patient's eye relative to the emitted laser pulses. A dedicated support assembly and rigid support of optical path components, however, can add significant complexity and related cost to a laser eye surgery system. Additionally, the use of rigid support of optical path components and a dedicated patient support assembly can fail to preclude the possibility of some level of significant relative movement between the patient and the laser eye surgery system.

Thus, laser surgery systems with improved characteristics with respect to patient movement, and related methods, would be beneficial.

SUMMARY

Imaging systems and related methods are provided that can be used in suitable laser surgery systems such as, for example, laser eye surgery systems. In many embodiments, a system for imaging an eye of a patient is configured to accommodate relative movement of a patient while maintaining alignment between the patient's eye and a scanned electromagnetic radiation beam used at least in part to image the eye. In many embodiments, the imaging system is configured to be insensitive to optical path length variations induced by patient movement. By accommodating patient movement, additional system complexity and related cost associated with attempting to restrain movement of the patient can be avoided. Additionally, accommodation of patient movement can be employed to increase ease of use of a laser surgery system, such as by configuring the laser surgery system to be supported by a repositionable cart that can be moved adjacent to an existing patient support assembly (e.g., a non-dedicated patient support assembly such as a bed).

Thus, in one aspect, a method of imaging an eye while accommodating patient movement is provided. The method includes using a beam source to generate an electromagnetic radiation beam. The electromagnetic radiation beam is propagated from the beam source to a scanner along a variable optical path having an optical path length that varies in response to movement of the eye. The electromagnetic radiation beam is focused to a focal point at a location within the eye. The scanner is used to scan the focal point to different locations within the eye. A portion of the electromagnetic radiation beam reflected from the focal point location is propagated back along the variable optical path to a sensor. The sensor is used to generate an intensity signal indicative of the intensity of a portion of the electromagnetic radiation beam reflected from the focal point location and propagated to the sensor.

In many embodiments of the method, one or more optical path related components are used to accommodate patient movement. For example, the method can further include using a first support assembly to support the scanner so as to accommodate relative movement between the scanner and the first support assembly so as to accommodate movement of the eye. The method can include using a second support assembly to support the first support assembly so as to accommodate relative movement between the first support assembly and the second support assembly so as to accommodate movement of the eye. The method can include using the first support assembly to support a first reflector configured to reflect the electromagnetic radiation beam so as to propagate to the scanner along a portion of the variable optical path. The method can include using a base assembly to support the second support assembly so as to accommodate relative movement between the second support assembly and the base assembly so as to accommodate movement of the eye. The method can include using the second support assembly to support a second reflector configured to reflect the electromagnetic radiation beam to propagate along a portion of the variable optical path so as to be incident on the first reflector.

In many embodiments of the method, portions of the electromagnetic radiation beam reflected from locations other than the focal point are blocked to ensure that only a portion of the electromagnetic beam reflected from the focal point is used to generate the intensity signal. For example, using the sensor to generate the intensity signal can include passing a reflected portion of the electromagnetic radiation beam through an aperture to block portions of the electromagnetic radiation beam reflected from locations other than the focal point location.

A polarization-sensitive device (e.g., a polarization beam splitter/combiner) can be used to direct a portion of the electromagnetic radiation beam reflected from the focal point to be incident upon a detector configured to generate the intensity signal. For example, the method can further include passing the electromagnetic radiation beam through a polarization-sensitive device. The method can further include modifying polarization of at least one of the electromagnetic radiation beam and a portion of the electromagnetic radiation beam reflected from the focal point location. The method can further include using the polarization-sensitive device to reflect a portion of the electromagnetic radiation beam reflected from the focal point location so as to be incident upon the sensor.

In many embodiments of the method, the electromagnetic radiation beam can be configured to so as to not modify tissue. For example, the electromagnetic radiation beam can have an energy level below a threshold level for tissue modification. Alternatively, the electromagnetic radiation beam can be configured to modify tissue.

The electromagnetic radiation beam can have any suitable configuration. For example, the electromagnetic radiation beam can include a plurality of laser pulses having a wavelength between 320 nanometers and 430 nanometers. As another example, the electromagnetic radiation beam can include a plurality of laser pulses having a wavelength between 800 nanometers and 1100 nanometers.

In another aspect, an eye surgery system is provided. The system includes an eye interface device, a scanning assembly, a beam source, a free-floating mechanism, and a detection assembly. The eye interface device is configured to interface with an eye of a patient. The scanning assembly supports the eye interface device and is operable to scan a focal point of an electromagnetic radiation beam to different locations within the eye. The beam source is configured to generate the electromagnetic radiation beam. The free-floating mechanism supports the scanning assembly and is configured to accommodate movement of the eye and provide a variable optical path for the electronic radiation beam and a portion of the electronic radiation beam reflected from the focal point location. The variable optical path is disposed between the beam source and the scanner and has an optical path length that changes in response to movement of the eye. The detection assembly is configured to generate an intensity signal indicative of intensity of a portion of the electromagnetic radiation beam reflected from the focal point location.

In many embodiments of the system, the scanning assembly includes one or more scanning devices. For example, the scanning assembly can include a z-scan device and a xy-scan device. The z-scan device can be operable to vary the location of the focal point in the direction of propagation of the electromagnetic radiation beam. The xy-scan device can be operable to vary the location of the focal point transverse to the direction of propagation of the electromagnetic radiation beam.

In many embodiments of the system, the free-floating mechanism includes beam deflection devices. For example, the free-floating mechanism can include a first beam deflection device and a second beam deflection device. The first beam deflection device can be configured to deflect the electromagnetic radiation beam propagating in a first direction to propagate in a second direction different from the first direction. The second beam deflection device can be configured to deflect the electromagnetic radiation beam propagating in the second direction to propagate in a third direction different from the second direction. The first beam deflection device can also be configured to deflect a portion of the electromagnetic radiation beam reflected from the focal point location and propagating opposite to the third direction to propagate opposite to the second direction. The second beam deflection device can also be configured to deflect a portion of the electromagnetic radiation beam reflected from the focal point and propagating opposite to the second direction to propagate opposite to the first direction. At least one of (1) a distance between the first and second beam deflection devices and (2) a rotational orientation between the first and second beam deflection devices can be varied to accommodate movement of the eye.

The free-floating mechanism can include a third beam deflection device. The third beam deflection device can be configured to deflect the electromagnetic radiation beam propagating in the third direction to propagate in a fourth direction different from the third direction. The third beam deflection device can also be configured to deflect a portion of the electromagnetic radiation beam reflected from the focal point location and propagating opposite to the fourth direction to propagate opposite to the third direction. At least one of (1) a distance between the second and third beam deflection devices and (2) a rotational orientation between the second and third beam deflection devices can be varied to accommodate movement of the eye.

In many embodiments of the system, the detection assembly includes a sensor configured to generate the intensity signal. The detection assembly can include an aperture configured to block portions of the electromagnetic radiation beam reflected from locations other than the focal point from reaching the sensor.

In many embodiments, the system includes a polarization-sensitive device and a polarizing device. The polarization-sensitive device can be disposed along an optical path of the electromagnetic radiation beam between the beam source and the free-floating mechanism. The electromagnetic radiation beam can pass through the polarization-sensitive device during propagation of the electromagnetic radiation beam from the beam source to the free-floating device. The polarizing device can be used to modify polarization of at least one of the electromagnetic radiation beam and a portion of the electromagnetic radiation beam reflected from the focal point location. The polarization-sensitive device can reflect a portion of the electromagnetic radiation beam reflected from the focal point so as to incident upon a sensor configured to generate the intensity signal. The polarizing device can include, for example, a one-quarter wave plate.

In many embodiments of the system, the electromagnetic radiation beam can be configured to so as to not modify tissue. For example, the electromagnetic radiation beam can have an energy level below a threshold level that would modify tissue. Alternatively, the electromagnetic radiation beam can be configured to modify tissue.

The electromagnetic radiation beam can have any suitable configuration. For example, the electromagnetic radiation beam can include a plurality of laser pulses having a wavelength between 320 nanometers and 430 nanometers. As another example, the electromagnetic radiation beam can include a plurality of laser pulses having a wavelength between 800 nanometers and 1100 nanometers. As a further example, the electromagnetic radiation beam can include a plurality of laser pulses having a pulse duration of between 100 femtoseconds and 15 nanoseconds.

For a fuller understanding of the nature and advantages of the present invention, reference should be made to the ensuing detailed description and accompanying drawings. Other aspects, objects and advantages of the invention will be apparent from the drawings and detailed description that follows.

INCORPORATION BY REFERENCE

All publications, patents, and patent applications mentioned in this specification are herein incorporated by reference in their entirety to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 5, 6, and 7 are simplified block diagrams of optional acts, in accordance with many embodiments, that can be accomplished in the method of FIG. 4.

FIG. 45 illustrates lens fragmentation patterns, in accordance with many embodiments.

DETAILED DESCRIPTION

In the following description, various embodiments of the present invention will be described. For purposes of explanation, specific configurations and details are set forth in order to provide a thorough understanding of the embodiments. It will also, however, be apparent to one skilled in the art that the present invention can be practiced without the specific details. Furthermore, well-known features may be omitted or simplified in order not to obscure the embodiment being described.

Systems for imaging and/or treating an eye of a patient are provided. In many embodiments, a free-floating mechanism provides a variable optical path by which a portion of an electromagnetic beam reflected from a focal point disposed within the eye is directed to a path length insensitive imaging assembly, such as a confocal detection assembly. In many embodiments, the free-floating mechanism is configured to accommodate movement of the patient while maintaining alignment between an electromagnetic radiation beam and the patient. The electromagnetic radiation beam can be configured for imaging the eye, can be configured for treating the eye, and can be configured for imaging and treating the eye.

Figure 1:
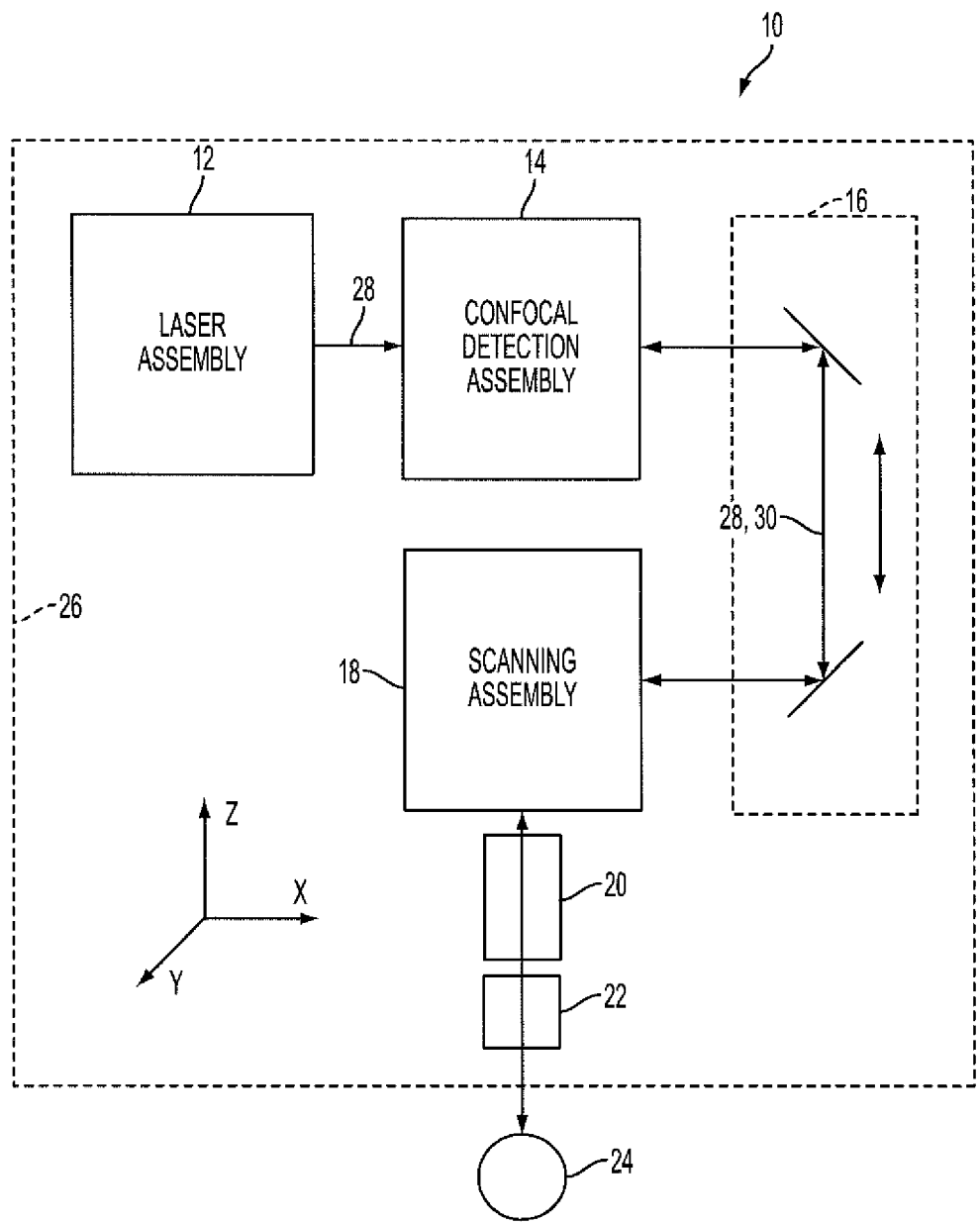
FIG. 1 is a schematic diagram of a laser surgery system, in accordance with many embodiments, in which a patient interface device is coupled to a laser assembly and a detection assembly by way of a scanning assembly and free-floating mechanism that supports the scanning assembly.

Referring now to the drawings in which like numbers reference similar elements, FIG. 1 schematically illustrates a laser surgery system 10, in accordance with many embodiments. The laser surgery system 10 includes a laser assembly 12, a confocal detection assembly 14, a free-floating mechanism 16, a scanning assembly 18, an objective lens assembly 20, and a patient interface device 22. The patient interface device 22 is configured to interface with a patient 24. The patient interface device 22 is supported by the objective lens assembly 20. The objective lens assembly 20 is supported by the scanning assembly 18. The scanning assembly 18 is supported by the free-floating mechanism 16. The free-floating mechanism 16 has a portion having a fixed position and orientation relative to the laser assembly 12 and the confocal detection assembly 14.

In many embodiments, the patient interface device 22 is configured to interface with an eye of the patient 24. For example, the patient interface device 22 can be configured to be vacuum coupled to an eye of the patient 24 such as described in co-pending U.S. Provisional Patent Application Ser. No. 61/721,693, entitled "Liquid Optical Interface for Laser Eye Surgery System", filed Nov. 2, 2012. The laser surgery system 10 can further optionally include a base assembly 26 that can be fixed in place or repositionable. For example, the base assembly 26 can be supported by a support linkage that is configured to allow selective repositioning of the base assembly 26 relative to a patient and secure the base assembly 26 in a selected fixed position relative to the patient. Such a support linkage can be supported in any suitable manner such as, for example, by a fixed support base or by a movable cart that can be repositioned to a suitable location adjacent to a patient. In many embodiments, the support linkage includes setup joints with each setup joint being configured to permit selective articulation of the setup joint and can be selectively locked to prevent inadvertent articulation of the setup joint, thereby securing the base assembly 26 in a selected fixed position relative to the patient when the setup joints are locked.

In many embodiments, the laser assembly 12 is configured to emit an electromagnetic radiation beam 28. The beam 28 can include a series of laser pulses of any suitable energy level, duration, and repetition rate.

In many embodiments, the laser assembly 12 incorporates femtosecond (FS) laser technology. By using femtosecond laser technology, a short duration (e.g., approximately $10^{-13}$ seconds in duration) laser pulse (with energy level in the micro joule range) can be delivered to a tightly focused point to disrupt tissue, thereby substantially lowering the energy level required to image and/or modify an intraocular target as compared to laser pulses having longer durations.

The laser assembly 12 can produce laser pulses having a wavelength suitable to treat and/or image tissue. For example, the laser assembly 12 can be configured to emit an electromagnetic radiation beam 28 such as emitted by any of the laser surgery systems described in copending U.S. Provisional Patent Application Ser. No. 61/722,048, entitled "Laser Eye Surgery System", filed Nov. 2, 2012; and U.S. patent application Ser. No. 12/987,069, entitled "Method and System For Modifying Eye Tissue and Intraocular Lenses", filed Jan. 7, 2011. For example, the laser assembly 12 can produce laser pulses having a wavelength from 1020 nm to 1050 nm. For example, the laser assembly 12 can have a diode-pumped solid-state configuration with a 1030 (+/−5) nm center wavelength. As another example, the laser assembly 12 can produce laser pulses having a wavelength 320 nm to 430 nm. For example, the laser assembly 12 can include an Nd:YAG laser source operating at the 3rd harmonic wavelength (355 nm) and producing pulses having 50 pico second to 15 nano second pulse duration. Depending on the spot size, typical pulse energies used can be in the nano joule to micro joule range. The laser assembly 12 can also include two or more lasers of any suitable configuration.

The laser assembly 12 can include control and conditioning components. For example, such control components can include components such as a beam attenuator to control the energy of the laser pulse and the average power of the pulse train, a fixed aperture to control the cross-sectional spatial extent of the beam containing the laser pulses, one or more power monitors to monitor the flux and repetition rate of the beam train and therefore the energy of the laser pulses, and a shutter to allow/block transmission of the laser pulses. Such conditioning components can include an adjustable zoom assembly and a fixed optical relay to transfer the laser pulses over a distance while accommodating laser pulse beam positional and/or directional variability, thereby providing increased tolerance for component variation.

In many embodiments, the laser assembly 12 and the confocal detection assembly 14 have fixed positions relative to the base assembly 26. The beam 28 emitted by the laser assembly 12 propagates along a fixed optical path through the confocal detection assembly 14 to the free-floating mechanism 16. The beam 28 propagates through the free-floating mechanism 16 along a variable optical path 30, which delivers the beam 28 to the scanning assembly 18. In many embodiments, the beam 28 emitted by the laser assembly 12 is collimated so that the beam 28 is not impacted by patient movement induced changes in the length of the optical path between the laser assembly 12 and the scanner 16. The scanning assembly 18 is operable to scan the beam 28 (e.g., via controlled variable deflection of the beam 28) in at least one dimension. In many embodiments, the scanning assembly 18 is operable to scan the beam 28 in two dimensions transverse to the direction of propagation of the beam 28 and is further operable to scan the location of a focal point of the beam 28 in the direction of propagation of the beam 28. The scanned beam is emitted from the scanning assembly 18 to propagate through the objective lens assembly 20, through the interface device 22, and to the patient 24.

The free-floating mechanism 16 is configured to accommodate a range of movement of the patient 24 relative to the laser assembly 12 and the confocal detection assembly 14 in one or more directions while maintaining alignment of the beam 28 emitted by the scanning assembly 18 with the patient 24. For example, in many embodiments, the free-floating mechanism 16 is configured to accommodate a range movement of the patient 24 in any direction defined by any combination of unit orthogonal directions (X, Y, and Z).

The free-floating mechanism 16 supports the scanning assembly 18 and provides the variable optical path 30, which changes in response to movement of the patient 24. Because the patient interface device 22 is interfaced with the patient 24, movement of the patient 24 results in corresponding movement of the patient interface device 22, the objective lens assembly 20, and the scanning assembly 18. The free-floating mechanism 16 can include, for example, any suitable combination of a linkage that accommodates relative movement between the scanning assembly 18 and, for example, the confocal detection assembly 24, and optical components suitably tied to the linkage so as to form the variable optical path 30.

A portion of the electromagnetic radiation beam 28 that is reflected by eye tissue at the focal point propagates back to the confocal detection assembly 14. Specifically, a reflected portion of the electromagnetic radiation beam 28 travels back through the patient interface device 22, back through the objective lens assembly 20, back through (and de- scanned by) the scanning assembly 18, back through the free-floating mechanism 16 (along the variable optical path 30), and to the confocal detection assembly 14. In many embodiments, the reflected portion of the electromagnetic radiation beam that travels back to the confocal detection assembly 14 is directed to be incident upon a sensor that generates an intensity signal indicative of intensity of the incident portion of the electromagnetic radiation beam. The intensity signal, coupled with associated scanning of the focal point within the eye, can be processed in conjunction with the parameters of the scanning to, for example, image/locate structures of the eye, such as the anterior surface of the cornea, the posterior surface of the cornea, the iris, the anterior surface of the lens capsule, and the posterior surface of the lens capsule. In many embodiments, the amount of the reflected electromagnetic radiation beam that travels to the confocal detection assembly 14 is substantially independent of expected variations in the length of the variable optical path 30 due to patient movement, thereby enabling the ability to ignore patient movements when processing the intensity signal to image/locate structures of the eye.

Figure 2:
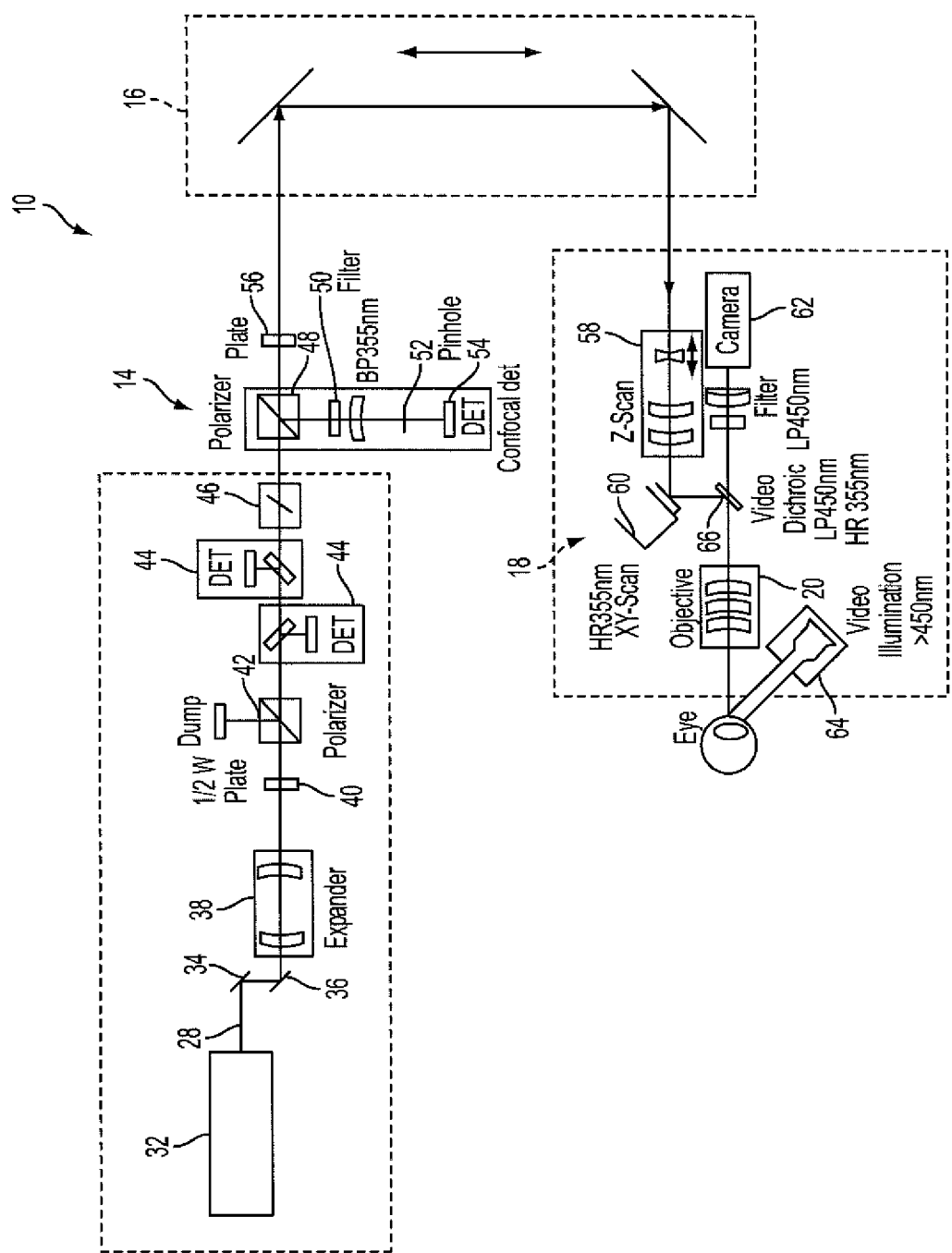
FIG. 2 is a schematic diagram of an embodiment of the laser surgery system of FIG. 1.

FIG. 2 schematically illustrates details of an embodiment of the laser surgery system 10. Specifically, example configurations are schematically illustrated for the laser assembly 12, the confocal detection assembly 14, and the scanning assembly 18. As shown in the illustrated embodiment, the laser assembly 12 can include an ultrafast (UF) laser 32 (e.g., a femtosecond laser), alignment mirrors 34, 36, a beam expander 38, a one-half wave plate 40, a polarizer and beam dump device 42, output pickoffs and monitors 44, and a system-controlled shutter 46. The electromagnetic radiation beam 28 output by the laser 32 is deflected by the alignment mirrors 34, 36. In many embodiments, the alignment mirrors 34, 36 are adjustable in position and/or orientation so as to provide the ability to align the beam 28 with the downstream optical path through the downstream optical components. Next, the beam 28 passes through the beam expander 38, which increases the diameter of the beam 28. Next, the expanded beam 28 passes through the one-half wave plate 40 before passing through the polarizer. The beam exiting the laser is linearly polarized. The one-half wave plate 40 can rotate this polarization. The amount of light passing through the polarizer depends on the angle of the rotation of the linear polarization. Therefore, the one-half wave plate 40 with the polarizer acts as an attenuator of the beam 28. The light rejected from this attenuation is directed into the beam dump. Next, the attenuated beam 28 passes through the output pickoffs and monitors 44 and then through the system-controlled shutter 46. By locating the system-controlled shutter 46 downstream of the output pickoffs and monitors 44, the power of the beam 28 can be checked before opening the system-controlled shutter 46.

As shown in the illustrated embodiment, the confocal detection assembly 14 can include a polarization-sensitive device such as a polarized or unpolarized beam splitter 48, a filter 50, a focusing lens 51, a pinhole aperture 52, and a detection sensor 54. A one-quarter wave plate 56 is disposed downstream of the polarized beam splitter 48. The beam 28 as received from the laser assembly 12 is polarized so as to pass through the polarized beam splitter 48. Next, the beam 28 passes through the one-quarter wave plate 56, thereby rotating the polarization axis of the beam 28. A quarter rotation is a presently preferred rotation amount. After reflecting from the focal point in the eye, the returning reflected portion of the beam 28 passes back through the one-quarter wave plate 56, thereby further rotating the polarization axis of the returning reflected portion of the beam 28. Ideally, after passing back through the one-quarter wave plate 56, the returning reflected portion of the beam has experienced a total polarization rotation of 90 degrees so that the reflected light from the eye is fully reflected by the polarized beam splitter 48. The birefringence of the cornea can also be taken into account if, for example, the imaged structure is the lens. In such a case, the plate 56 can be adjusted/configured so that the double pass of the plate 56 as well as the double pass of the cornea sum up to a polarization rotation of 90 degrees. Because the birefringence of the cornea may be different form patient to patient, the configuration/adjustment of the plate 56 can be done dynamically so as to optimize the signal returning to the detection sensor 54. Accordingly, the returning reflected portion of the beam 28 is now polarized to be at least partially reflected by the polarized beam splitter 48 so as to be directed through the filter 50, through the lens 51, and to the pinhole aperture 52. The filter 50 can be configured to block wavelengths other than the wavelengths of interest. The pinhole aperture 52 is configured to block any returning reflected portion of the beam 28 reflected from locations other than the focal point from reaching the detection sensor 54. Because the amount of returning reflected portion of the beam 28 that reaches the detection sensor 54 depends upon the nature of the tissue at the focal point of the beam 28, the signal generated by the detection sensor 54 can be processed in combination with data regarding the associated locations of the focal point so as to generate image/location data for structures of the eye.

As shown in the illustrated embodiment, the scanning assembly 18 can include a z-scan device 58 and a xy-scan device 60. The z-scan device 58 is operable to vary a convergence/divergence angle of the beam 28 and thereby change a location of the focal point in the direction of propagation of the beam 28. For example, the z-scan device 58 can include one or more lenses that are controllably movable in the direction of propagation of the beam 28 to vary a convergence/divergence angle of the beam 28. The xy-scan device 60 is operable to deflect the beam 28 in two dimensions transverse to the direction of propagation of the beam 28. For example, the xy-scan device 60 can include one or more mirrors that are controllably deflectable to scan the beam 28 in two dimensions transverse to the direction of propagation of the beam 28. Accordingly, the combination of the z-scan device 58 and the xy-scan device 60 can be operated to controllably scan the focal point in three dimensions, for example, within the eye of the patient.

As shown in the illustrated embodiment, a camera 62 and associated video illumination 64 can be integrated with the scanning assembly 18. The camera 62 and the beam 28 share a common optical path through the objective lens assembly 20 to the eye. A video dichroic 66 is used to combine/separate the beam 28 with/from the illumination wavelengths used by the camera. For example, the beam 28 can have a wavelength of about 355 nm and the video illumination 64 can be configured to emit illumination having wavelengths greater than 450 nm. Accordingly, the video dichroic 66 can be configured to reflect the 355 nm wavelength while transmitting wavelengths greater than 450 nm.

Figure 3A:
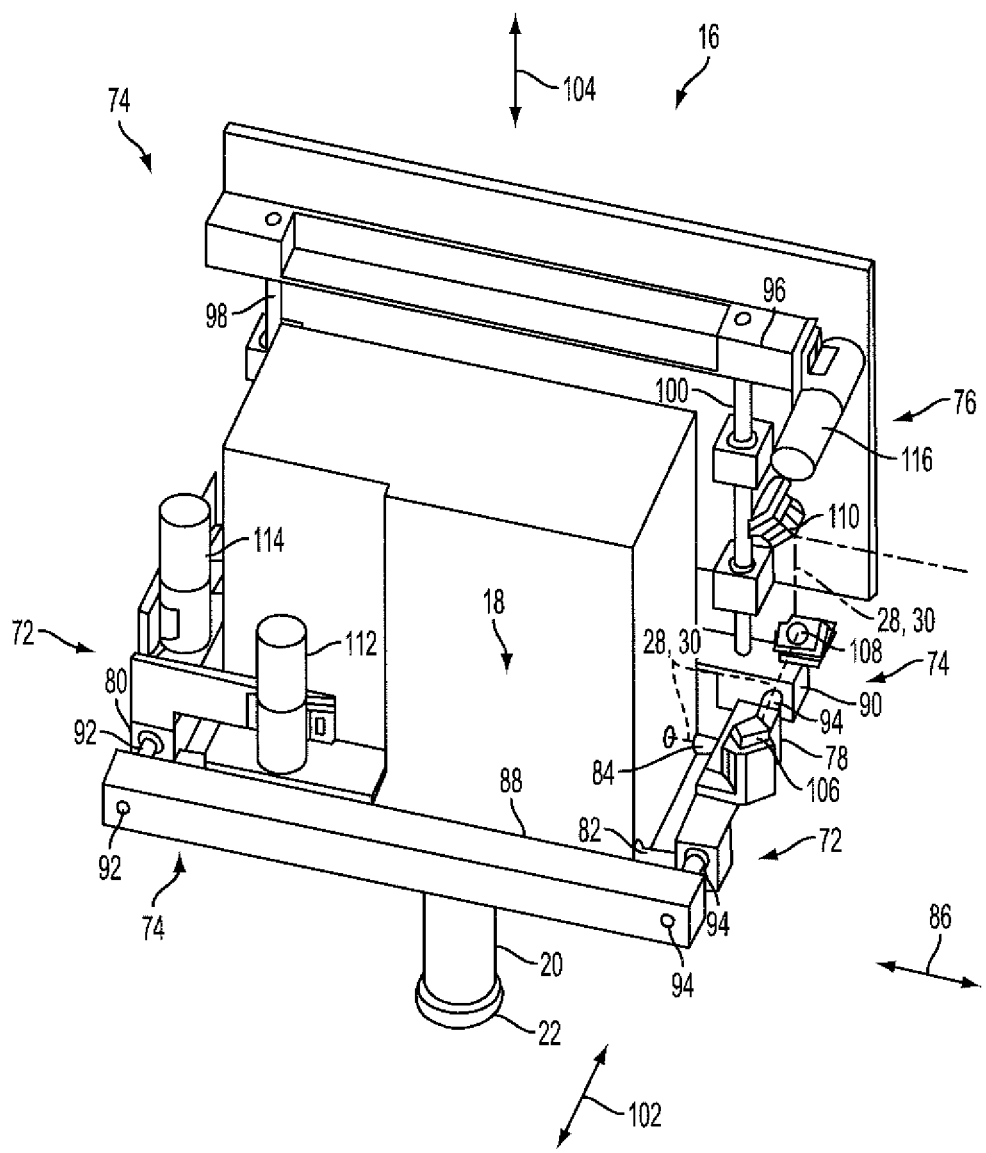
FIG. 3A shows an isometric view of an embodiment of the free-floating mechanism and scanning assembly of FIG. 1.

FIG. 3A shows an example embodiment of the free-floating mechanism 16 (shown supporting a scanning assembly 18, an objective lens assembly 20, and a patient interface device 22) to illustrate a suitable linkage that accommodates relative movement between the scanning assembly 18 and the confocal detection assembly 14. Optical components are coupled with associated links of the linkage so as to form the variable optical path 30. The free-floating mechanism 16 includes a first support assembly 72, a second support assembly 74, and a base assembly 76. The eye interface device 22 is coupled with and supported by the objective lens assembly 20. The objective lens assembly 20 is coupled with and supported by the scanning assembly 18. The combination of the interface device 22, the objective lens assembly 20, and the scanning assembly 18 form a unit that moves in unison in response to movement of the patient.

The first support assembly 72 includes a first end frame 78, a second end frame 80, and transverse rods 82, 84, which extend between and couple to the end frames 78, 80. The transverse rods 82, 84 are oriented parallel to a first direction 86. The scanning assembly 18 is supported by the transverse rods 82, 84 and slides along the rods 82, 84 in response to patient movement parallel to the first direction 86. The transverse rods 82, 84 form part of a linear bearing accommodating patient movement parallel to the first direction 86.

The second support assembly 74 includes a first end frame 88, an intermediate frame 90, transverse rods 92, 94, a second end frame 96, and vertical rods 98, 100. The transverse rods 92, 94 extend between and couple to the first end frame 88 and to the intermediate frame 90. The transverse rods 92, 94 are oriented parallel to a second direction 102, which is at least transverse to and can be orthogonal to the first direction 86. Each of the first and second directions 86, 102 can be horizontal. The first support assembly 72 is supported by the transverse rods 92, 94 and slides along the rods 92, 94 in response to patient movement parallel to the second direction 102. The transverse rods 92, 94 form part of a linear bearing accommodating patient movement parallel to the second direction 102. The vertical rods 98, 100 extend between and couple to the intermediate frame 90 and to the second end frame 96. The vertical rods 98, 100 are oriented parallel to a third direction 104, which is at least transverse to each of first and second directions 86, 102, and can be orthogonal to at least one of the first and second directions 86, 102. The vertical rods 98, 100 form part of a linear bearing accommodating relative movement between the second support assembly 74 and the base assembly 76 parallel to the third direction 104, thereby accommodating patient movement parallel to the third direction 104.

First, second, and third reflectors 106, 108, 110 (e.g., mirrors) are supported by the free-floating mechanism 16 and configured to reflect the electromagnetic radiation beam 28 to propagate along the variable optical path 30. The first reflector 106 is mounted to the first support assembly 72 (to the first end frame 78 in the illustrated embodiment). The second reflector 108 is mounted to the second support assembly 74 (to the intermediate frame 90 in the illustrated embodiment). The third reflector 110 is mounted to the base assembly 76. In operation, the beam 28 emitted by the laser assembly is deflected by the third reflector 110 so as to propagate parallel to the third direction 104 and be incident upon the second reflector 108. The second reflector 108 deflects the beam 28 so as to propagate parallel to the second direction 102 and be incident upon the first reflector 106. The first reflector 106 deflects the beam 28 so as to propagate parallel to the first direction 86 and into the scanning assembly 18, which then controllably scans and outputs the scanned beam through the objective lens assembly 20 and the eye interface device 22. By propagating the beam 28 parallel to the third direction 104 from the third reflector 110 to the second reflector 108, the length of the corresponding portion of the variable optical path 30 can be varied so as to accommodate relative movement of the patient relative to the third direction 104. By propagating the beam 28 parallel to the second direction 102 from the second reflector 108 to the first reflector 106, the length of the corresponding portion of the variable optical path 30 can be varied so as to accommodate relative movement of the patient relative to the second direction 102. By propagating the beam 28 parallel to the first direction 86 from the first reflector 106 to the scanning assembly 18, the length of the corresponding portion of the variable optical path 30 can be varied so as to accommodate relative movement of the patient relative to the first direction 86.

In the illustrated embodiment, the free-floating mechanism 16 further includes a first solenoid brake assembly 112, a second solenoid brake assembly 114, and a third solenoid brake assembly 116. The solenoid brake assemblies 112, 114, 116 are operable to selectively prevent inadvertent articulation of the free-floating mechanism 16 during initial positioning of the laser surgery system 10 relative to a patient's eye. Inadvertent articulation of the free-floating mechanism 16 may occur, for example, when the laser surgery system 10 is initially repositioned to be in a suitable position relative to the patient. For example, in the absence of any mechanism for preventing inadvertent articulation of the free-floating mechanism 16, movement of the laser surgery system 10 may induce inadvertent articulation of the free-floating mechanism 16, especially when a user induces movement of the laser surgery system 10 through contact with, for example, the objective lens assembly 20 to move the objective lens assembly 20 into a suitable location relative to the patient. When the laser surgery system 10 is supported by a support linkage mechanism that includes setup joints, preventing inadvertent articulation of the free-floating mechanism 16 can be used to ensure that the initial positioning of the laser surgery system occurs via articulation of the setup joints instead of via articulation of the free-floating mechanism 16.

The first solenoid brake assembly 112 is configured to selectively prevent inadvertent movement between the scanning assembly 18 and the first support assembly 72. Engagement of the first solenoid brake assembly 112 prevents movement of the scanning assembly 18 along the transverse rods 82, 84, thereby preventing relative movement between the scanning assembly 18 and the first support assembly 72 parallel to the first direction 86. When the first solenoid brake assembly 112 is not engaged, the scanning assembly 18 is free to slide along the transverse rods 82, 84, thereby permitting relative movement between the scanning assembly 18 and the first support assembly 72 parallel to the first direction 86. In many embodiments, the free-floating mechanism 16 includes a detent mechanism and/or an indicator that is configured to permit engagement of the first solenoid brake assembly 112 when the scanning assembly 18 is centered relative to its range of travel along the transverse rods 82, 84, thereby ensuring equal range of travel of the scanning assembly 18 in both directions parallel to the first direction 86 when the first solenoid brake assembly 112 is disengaged following positioning of the objective lens assembly 20 relative to the patient.

The second solenoid brake assembly 114 is configured to selectively prevent inadvertent movement between the first support assembly 72 and the second support assembly 74. Engagement of the second solenoid brake assembly 114 prevents movement of the first support assembly 72 along the transverse rods 92, 94, thereby preventing relative movement between the first support assembly 72 and the second support assembly 74 parallel to the second direction 102. When the second solenoid brake assembly 114 is not engaged, the first support assembly 72 is free to slide along the transverse rods 92, 94, thereby permitting relative movement between the first support assembly 72 and the second support assembly 74 parallel to the second direction 102. In many embodiments, the free-floating mechanism 16 includes a detent mechanism and/or an indicator that is configured to permit engagement of the second solenoid brake assembly 114 when the first support assembly 72 is centered relative to its range of travel along the transverse rods 92, 94, thereby ensuring equal range of travel of the first support assembly 72 in both directions parallel to the second direction 102 when the second solenoid brake assembly 114 is disengaged following positioning of the objective lens assembly 20 relative to the patient.

The third solenoid brake assembly 116 is configured to selectively prevent inadvertent movement between the second support assembly 74 and the base assembly 76. Engagement of the third solenoid brake assembly 116 prevents movement of the base assembly 76 along the vertical rods 98, 100, thereby preventing relative movement between the second support assembly 74 and the base assembly 76 parallel to the third direction 104. When the third solenoid brake assembly 116 is not engaged, the base assembly 76 is free to slide along the vertical rods 98, 100, thereby permitting relative movement between the second support assembly 74 and the base assembly 76 parallel to the third direction 104. In many embodiments, the free-floating mechanism 16 includes a detent mechanism and/or an indicator that is configured to permit engagement of the third solenoid brake assembly 116 when the base assembly 76 is centered relative to its range of travel along the vertical rods 98, 100, thereby ensuring equal range of travel of the base assembly 72 in both directions parallel to the third direction 102 when the third solenoid brake assembly 116 is disengaged following positioning of the objective lens assembly 20 relative to the patient.

In an optional embodiment, the third reflector 110 is omitted and the incoming beam 28 is directed to propagate parallel to the third direction 104 so as to be incident on the second reflector 108. Each of the reflectors 106, 108, 110 can be adjustable in position and/or in orientation and thereby can be adjusted to align the corresponding portions of the variable optical path 30 with the first, second, and third directions 86, 102, 104, respectively. Accordingly, the use of the third reflector 110 can provide the ability to align the portion of the variable optical path 30 between the third reflector 110 and the second reflector 108 so as to be parallel to the third direction 104 and thereby compensate for relative positional and/or orientation variability between the laser assembly 12 and the free-floating mechanism 16.

In the illustrated embodiment of the free-floating mechanism 16, the first and second directions 86, 102 can be horizontal and the third direction 104 can be vertical. The free-floating mechanism 16 can also include a counter-balance mechanism configured to inhibit gravity-induced movement of the eye interface device 22 and/or transfer of gravity-induced force to an eye via the eye interface device 22. For example, a counter-balance mechanism can be employed to apply a counter-balancing vertical force to the second assembly 74, thereby inhibiting or even preventing gravity-induced relative movement between the second assembly 74 and the base assembly 76 and/or transfer of gravity-induced force to an eye via the eye interface device 22.

Other suitable variations of the free-floating mechanism 16 are possible. For example, the scanning assembly 18 can be slidably supported relative to a first support assembly via a vertically-oriented linear bearing. The first support assembly can be slidably supported relative to a second support assembly via a first horizontally-oriented linear bearing. The second support assembly can be slidably supported relative to a base assembly via a second horizontally-oriented linear bearing that is oriented transverse (e.g., perpendicular) to the first horizontally-oriented linear bearing. In such a configuration, a counter-balancing mechanism can be used to apply a counter-balancing force to the scanning assembly 18, thereby inhibiting or even preventing gravity-induced movement of the scanning assembly 18 and the eye interface device 22 and/or transfer of gravity-induced force to an eye coupled with the eye interface device 22. The free-floating mechanism 16 can also incorporate one or more sensors configured to monitor relative position (1) between the scanning assembly 18 and the first support assembly 72, (2) between the first support assembly 72 and the second support assembly 74, and/or (3) between the second support assembly 74 and the base assembly 76.

Figure 3B:
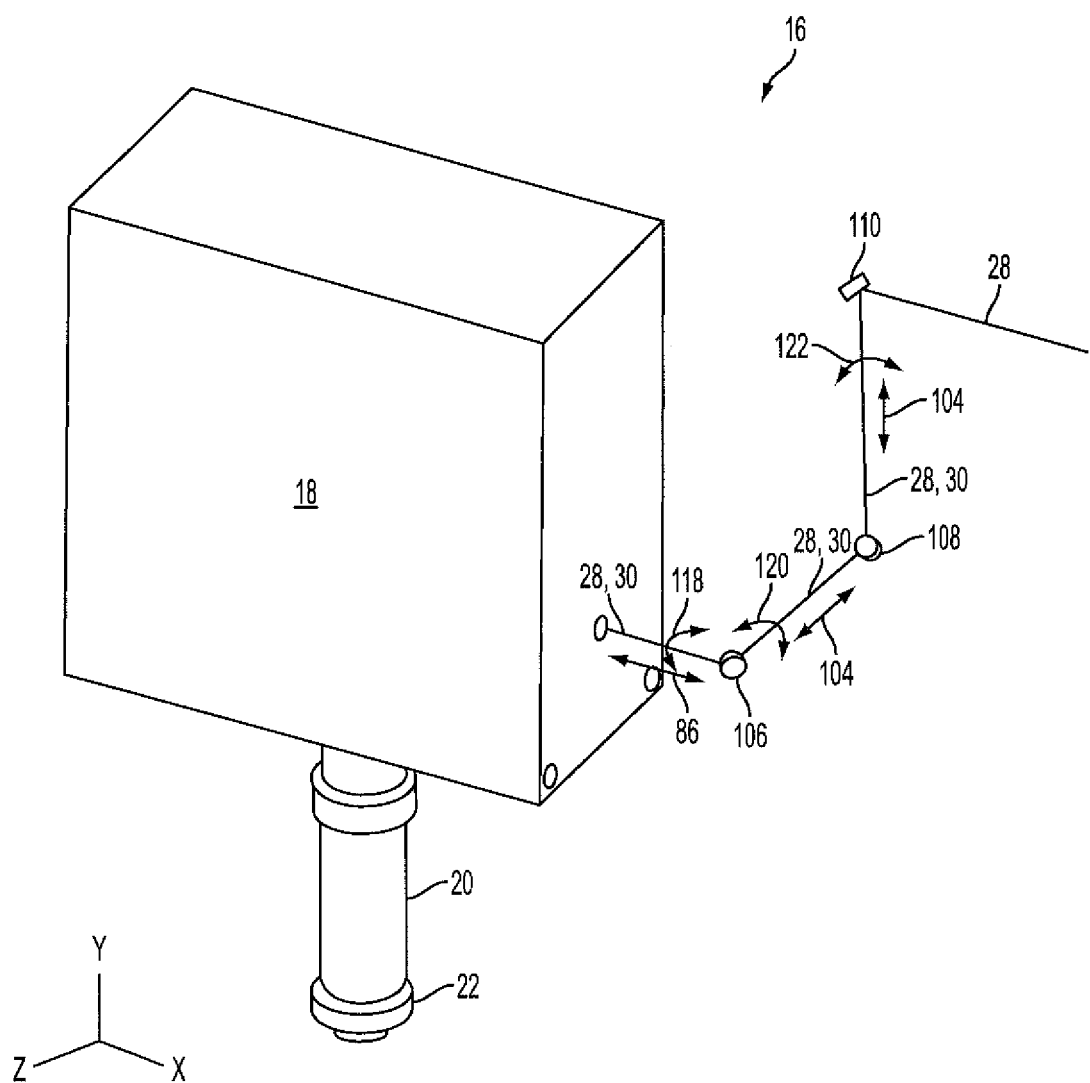
FIG. 3B schematically illustrates relative movements that can be used in embodiments of the free-floating mechanism and scanning assembly of FIG. 1.

FIG. 3B schematically illustrates relative movements that can be used in the free-floating mechanism 16 that can be used to accommodate patient movement, in accordance with many embodiments. The free-floating mechanism 16 includes the first reflector 106, the second reflector 108, and the third reflector 110. In many embodiments, the free-floating mechanism 16 includes a linkage assembly (not shown) that is configured to permit certain relative movement between the scanner 18 and the first reflector 106, between the first reflector 106 and the second reflector 108, and between the second reflector 108 and the third reflector 110 so as to consistently direct the electromagnetic radiation beam 28 to the scanner 18 while accommodating three-dimensional relative movement between the patient interface device 22 and the laser assembly generating the electromagnetic radiation beam 28. For example, similar to the embodiment of the free-floating mechanism 16 illustrated in FIG. 3A, a free-floating mechanism 16 can be configured such that the scanner 18 is supported by a first support assembly such that the scanner is free to translate relative to the first support assembly parallel to the first direction 86, thereby maintaining the location and orientation of the beam 28 between the first reflector 106 and the scanner 18. Likewise, the first support assembly can be supported by a second support assembly such that the first support assembly is free to translate relative to the second support assembly parallel to a second direction 102, thereby maintaining the location and orientation of the beam 28 between the second reflector 108 and the first reflector 106. And the second support assembly can be supported by a base assembly such that the second support assembly is free to translate relative to the base assembly parallel to a third direction 104, thereby maintaining the location and orientation of the beam 28 between the third reflector 110 and the second reflector 108.

The free-floating mechanism 16 can also employ one or more relative rotations so as to maintain the location and orientation of path segments of the beam 28. For example, the scanner 18 can be supported by a first support assembly such that the scanner is free to undergo a rotation 118 relative to the first support assembly about an axis coincident with the path segment of the beam 28 between the first reflector 106 and the scanner 18, thereby maintaining the location and orientation of the beam 28 between the first reflector 106 and the scanner 18. Likewise, the first support assembly can be supported by a second support assembly such that the first support assembly is free to undergo a rotation 120 relative to the second support assembly about an axis coincident with the path segment of the beam 28 between the second reflector 108 and the first reflector 106, thereby maintaining the location and orientation of the beam 28 between the second reflector 108 and the first reflector 106. And the second support assembly can be supported by a base assembly such that the second support assembly is free to undergo a rotation 122 relative to the base assembly about an axis coincident with the path segment of the beam 28 between the third reflector 110 and the second reflector 108, thereby maintaining the location and orientation of the beam 28 between the third reflector 110 and the second reflector 108.

The free-floating mechanism 16 can also employ any suitable combination of relative translations and relative rotations so as to maintain the location and orientation of path segments of the beam 28. For example, with respect to the configuration illustrated in FIG. 3B, the free-floating mechanism 16 can employ relative translation parallel to the second direction 102, relative translation parallel to the third direction 104, and relative rotation 122, thereby allowing three-dimensional movement of the patient interface 22 relative to the laser assembly used to generate the beam 28, and thereby accommodating patient movement.

Figure 4:
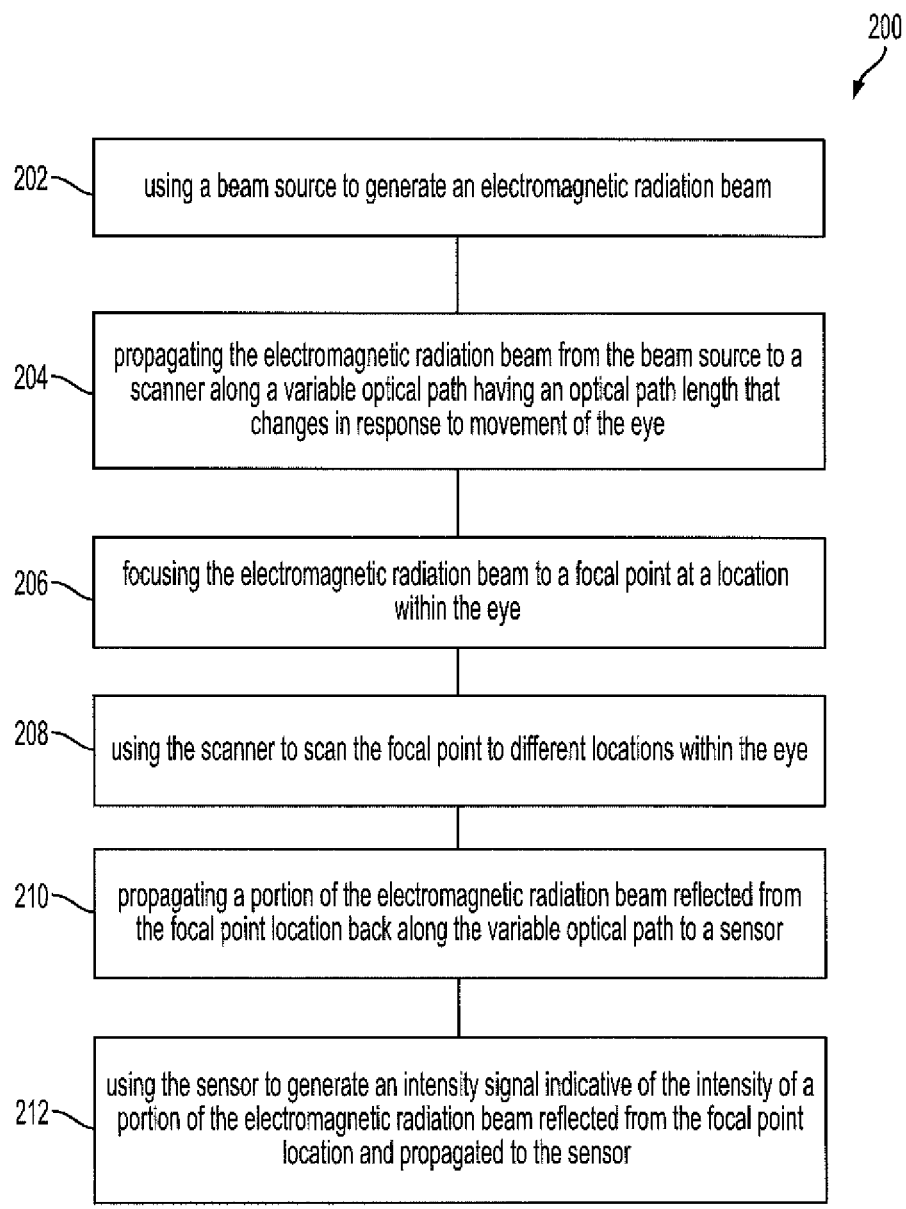
FIG. 4 is a simplified block diagrams of acts of a method, in accordance with many embodiments, of imaging and/or modifying an intraocular target.

FIG. 4 is a simplified block diagram of acts of a method 200, in accordance with many embodiments, of imaging an eye while accommodating patient movement. Any suitable device, assembly, and/or system, such as described herein, can be used to practice the method 200. The method 200 includes using a beam source to generate an electromagnetic radiation beam (act 202).

The method 200 includes propagating the electromagnetic radiation beam from the beam source to a scanner along a variable optical path having an optical path length that changes in response to movement of the eye (act 204). The method 200 includes focusing the electromagnetic radiation beam to a focal point at a location within the eye (act 206). The method 200 includes using the scanner to scan the focal point to different locations within the eye (act 208). The method 200 includes propagating a portion of the electromagnetic radiation beam reflected from the focal point location back along the variable optical path to a sensor (act 210). The method 200 includes using the sensor to generate an intensity signal indicative of the intensity of a portion of the electromagnetic radiation beam reflected from the focal point location and propagated to the sensor (act 212).

Figure 5:
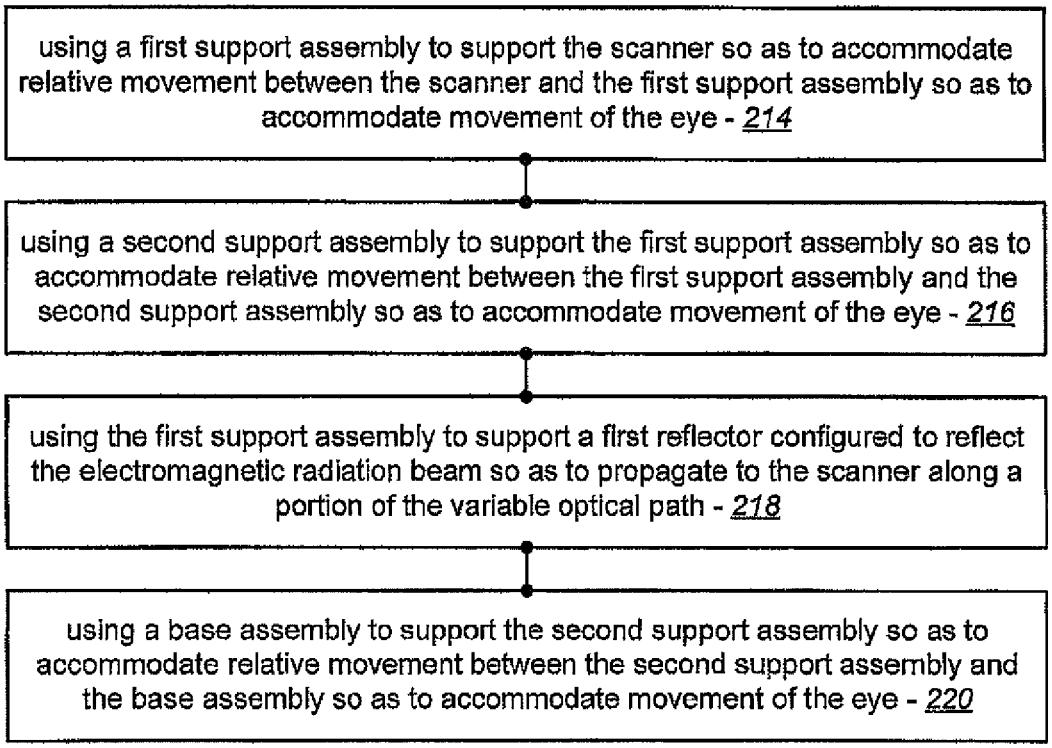

FIGS. 5, 6 and 7 are simplified block diagrams of optional acts that can be accomplished as part of the method 200. For example, the method 200 can include using a first support assembly to support the scanner so as to accommodate relative movement between the scanner and the first support assembly so as to accommodate movement of the eye (act 214). The method 200 can include using a second support assembly to support the first support assembly so as to accommodate relative movement between the first support assembly and the second support assembly so as to accommodate movement of the eye (act 216). The method 200 can include using the first support assembly to support a first reflector configured to reflect the electromagnetic radiation beam so as to propagate to the scanner along a portion of the variable optical path (act 218). The method 200 can include using a base assembly to support the second support assembly so as to accommodate relative movement between the second support assembly and the base assembly so as to accommodate movement of the eye (act 220). The method 200 can include using the second support assembly to support a second reflector configured to reflect the electromagnetic radiation beam to propagate along a portion of the variable optical path so as to be incident on the first reflector (act 222). The method 200 can include using the sensor to generate the intensity signal comprises passing a reflected portion of the electromagnetic radiation beam through an aperture to block portions of the electromagnetic radiation beam reflected from locations other than the focal point location (act 224). The method 200 can include passing the electromagnetic radiation beam through a polarization-sensitive device (act 226). The method 200 can include modifying polarization of at least one of the electromagnetic radiation beam and a portion of the electromagnetic radiation beam reflected from the focal point location (act 228). The method 200 can include using the polarization-sensitive device to reflect a portion of the electromagnetic radiation beam reflected from the focal point location so as to be incident upon the sensor (act 230).

Figure 8:
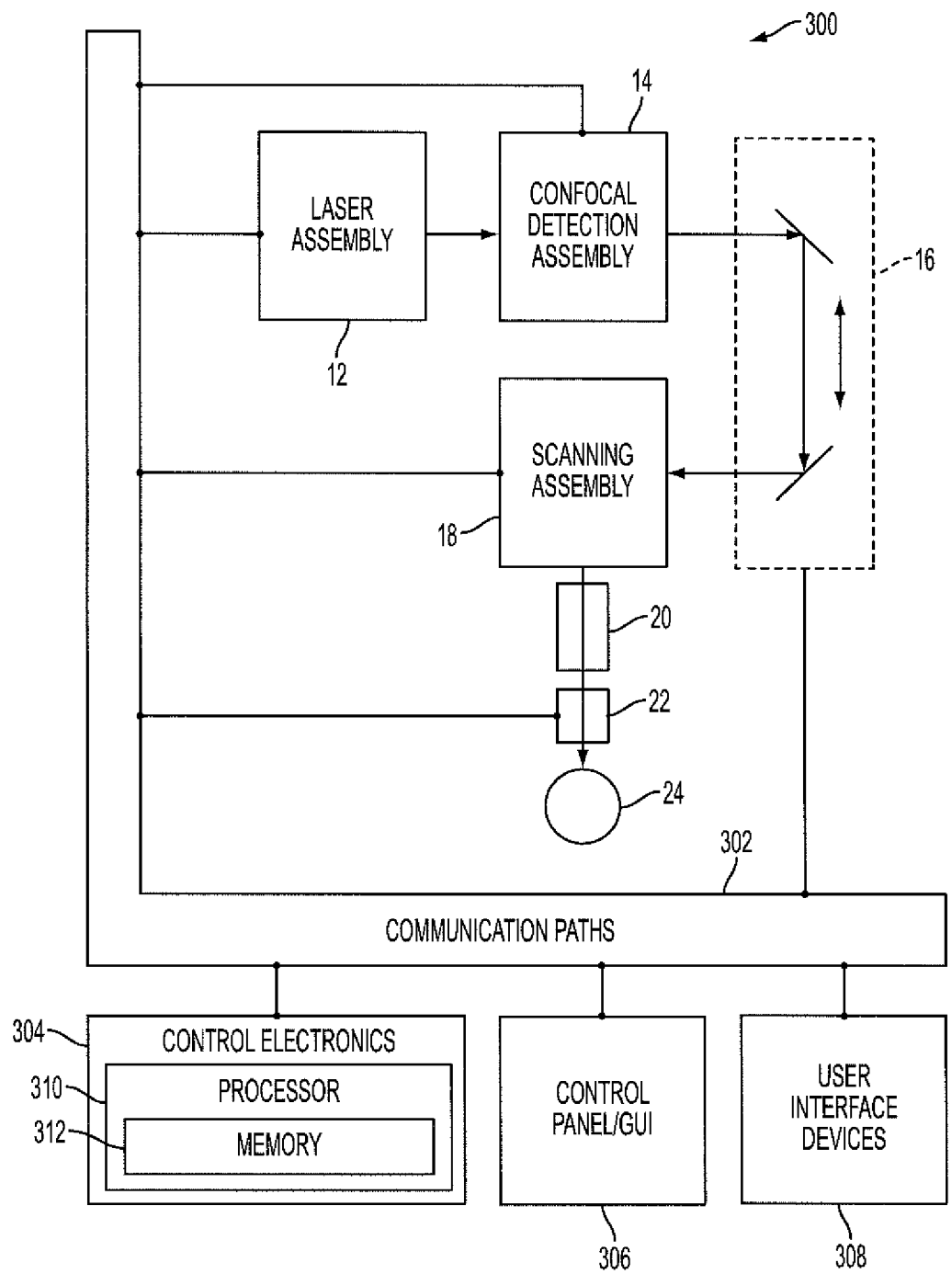
FIG. 8 is a schematic diagram of an embodiment of the laser surgery system of FIG. 1.

FIG. 8 schematically illustrates a laser surgery system 300, in accordance with many embodiments. The laser surgery system 300 includes the laser assembly 12, the confocal detection assembly 14, the free-floating mechanism 16, the scanning assembly 18, the objective lens assembly 20, the patient interface 22, communication paths 302, control electronics 304, control panel/graphical user interface (GUI) 306, and user interface devices 308. The control electronics 304 includes processor 310, which includes memory 312. The patient interface 22 is configured to interface with a patient 24. The control electronics 304 is operatively coupled via the communication paths 302 with the laser assembly 12, the confocal detection assembly 14, the free-floating mechanism 16, the scanning assembly 18, the control panel/GUI 306, and the user interface devices 308.

The free-floating mechanism 16 can be configured as illustrated in FIG. 3 to include, for example, the first reflector 106, the second reflector 108, and the third reflector 110. Accordingly, the free-floating mechanism 16 can be configured to accommodate movement of the patient 24 relative to the laser assembly 12 and the confocal detection assembly 14 in any direction resulting from any combination of three orthogonal unit directions.

The scanning assembly 18 can include a z-scan device and a xy-scan device. The laser surgery system 300 can be configured to focus the electromagnetic radiation beam 28 to a focal point that is scanned in three dimensions. The z-scan device can be operable to vary the location of the focal point in the direction of propagation of the beam 28. The xy-scan device can be operable to scan the location of the focal point in two dimensions transverse to the direction of propagation of the beam 28. Accordingly, the combination of the z-scan device and the xy-scan device can be operated to controllably scan the focal point of the beam in three dimensions, including within a tissue of the patient 24 such as within an eye tissue of the patient 24. As illustrated above and described with respect to FIG. 3, the scanning assembly 18 is supported by the free-floating mechanism 16, which accommodates patient movement induced movement of the scanning assembly 18 relative to the laser assembly 12 and the confocal detection assembly 14 in three dimensions.

The patient interface 22 is coupled to the patient 24 such that the patient interface 22, the objective lens assembly 20, and the scanning assembly 18 move in conjunction with the patient 24. For example, in many embodiments, the patient interface 22 employs a suction ring that is vacuum attached to an eye of the patient 24. The suction ring can be coupled with the patient interface 22, for example, using vacuum to secure the suction ring to the patient interface 22.

The control electronics 304 controls the operation of and/or can receive input from the laser assembly 12, the confocal detection assembly 14, the free-floating assembly 16, the scanning assembly 18, the patient interface 22, the control panel/GUI 306, and the user interface devices 308 via the communication paths 302. The communication paths 302 can be implemented in any suitable configuration, including any suitable shared or dedicated communication paths between the control electronics 304 and the respective system components.

The control electronics 304 can include any suitable components, such as one or more processor, one or more field-programmable gate array (FPGA), and one or more memory storage devices. In many embodiments, the control electronics 304 controls the control panel/GUI 306 to provide for pre-procedure planning according to user specified treatment parameters as well as to provide user control over the laser eye surgery procedure.

The control electronics 304 can include a processor/controller 310 that is used to perform calculations related to system operation and provide control signals to the various system elements. A computer readable medium 312 is coupled to the processor 310 in order to store data used by the processor and other system elements. The processor 310 interacts with the other components of the system as described more fully throughout the present specification. In an embodiment, the memory 312 can include a look up table that can be utilized to control one or more components of the laser system surgery system 300.

The processor 310 can be a general purpose microprocessor configured to execute instructions and data, such as a Pentium processor manufactured by the Intel Corporation of Santa Clara, Calif. It can also be an Application Specific Integrated Circuit (ASIC) that embodies at least part of the instructions for performing the method in accordance with the embodiments of the present disclosure in software, firmware and/or hardware. As an example, such processors include dedicated circuitry, ASICs, combinatorial logic, other programmable processors, combinations thereof, and the like.

The memory 312 can be local or distributed as appropriate to the particular application. Memory 312 can include a number of memories including a main random access memory (RAM) for storage of instructions and data during program execution and a read only memory (ROM) in which fixed instructions are stored. Thus, the memory 312 provides persistent (non-volatile) storage for program and data files, and may include a hard disk drive, flash memory, a floppy disk drive along with associated removable media, a Compact Disk Read Only Memory (CD-ROM) drive, an optical drive, removable media cartridges, and other like storage media.

The user interface devices 308 can include any suitable user input device suitable to provide user input to the control electronics 304. For example, the user interface devices 308 can include devices such as, for example, a touch-screen display/input device, a keyboard, a footswitch, a keypad, a patient interface radio frequency identification (RFID) reader, an emergency stop button, and a key switch.

System Calibration

The laser surgery system 10 can be calibrated to relate locations in a treatment space with pixels in the camera 62 and with control parameters used to control the scanning assembly 18 such that the focal point of the electromagnetic radiation beam can be accurately positioned within the intraocular target. Such calibration can be accomplished at any suitable time, for example, prior to using the laser surgery system 10 to treat a patient's eye.

Figure 9:
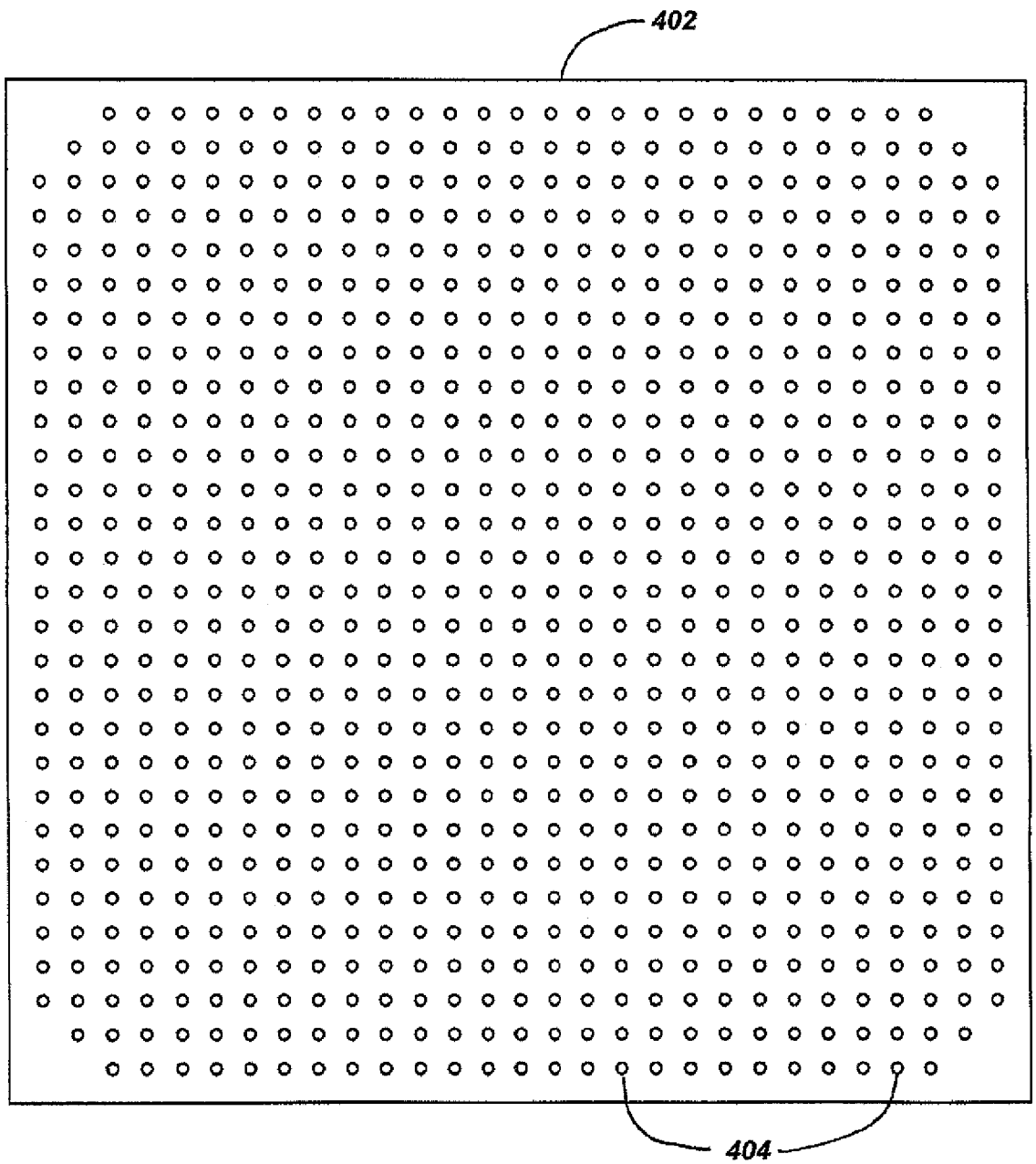
FIG. 9 is a plan view illustrating a calibration plate, in accordance with many embodiments, that can be used to calibrate the laser surgery system of FIG. 1.

FIG. 9 is a top view diagram of a calibration plate 402 that can be used to calibrate the laser surgery system 10. In many embodiments, the calibration plate 402 is a thin plate having an array of target features, for example, through holes 404 therein. In alternate embodiments, the calibration plate 402 is a thin plate having a field of small dots as the target features. While any suitable arrangement of the target features can be used, the calibration plate 402 of FIG. 9 has an orthogonal array of through holes 404. Any suitable number of the target features can be included in the calibration plate 402. For example, the illustrated embodiment has 29 rows and 29 columns of the through holes 404, with three through holes at each of the four corners of the calibration plate 402 being omitted from the orthogonal array of through holes 404.

In many embodiments, each of the through holes 404 is sized small enough to block a suitable portion of an electromagnetic radiation beam when the focal point of the electromagnetic radiation beam is not located at the through hole. For example, each of the through holes 404 can have a diameter slightly greater than the diameter of the focal point of the electromagnetic radiation beam so as to not block any of the electromagnetic radiation beam when the focal point is positioned at one of the through holes 404. In the embodiment shown, the through holes 404 have a diameter of 5 μm, which is sized to be used in conjunction with a focal point diameter of 1 μm.

Figure 10:
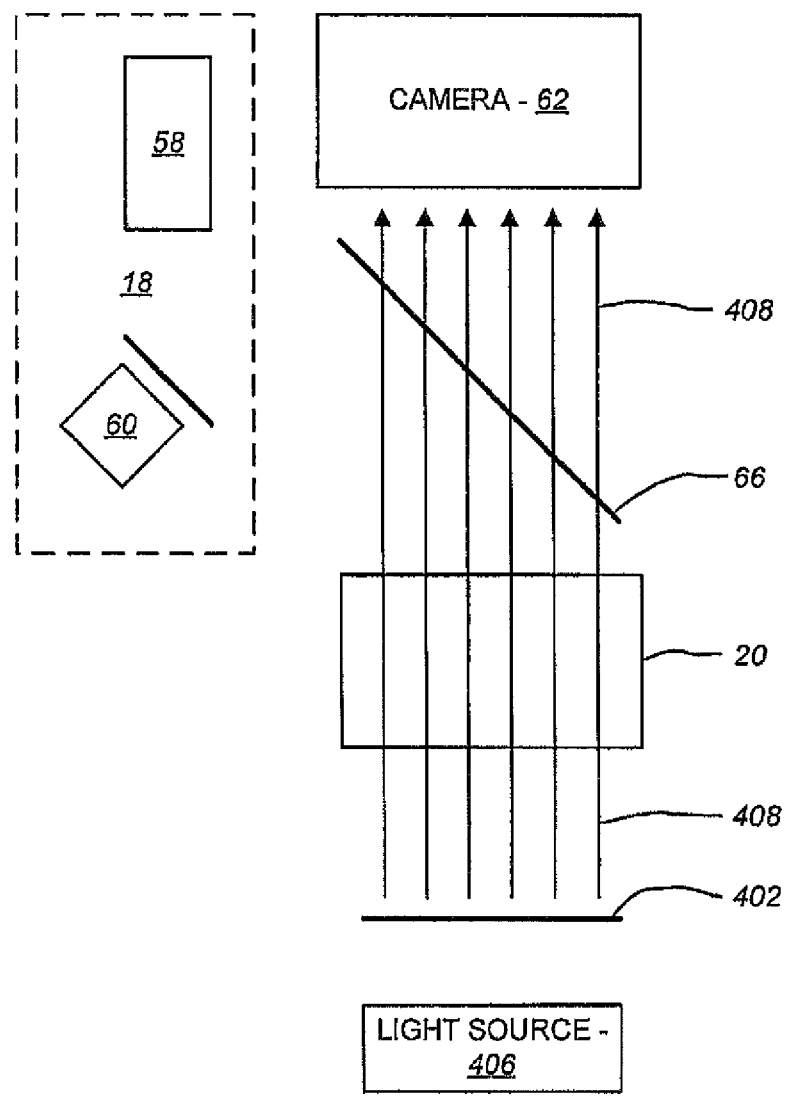
FIG. 10 is a schematic diagram illustrating using the calibration plate of FIG. 9 to calibrate a camera of the laser surgery system of FIG. 1.

FIG. 10 schematically illustrates using the calibration plate 402 to calibrate the camera 62 of the laser surgery system 10. The calibration plate 402 is supported at a known fixed location relative to the objective lens assembly 20. In many embodiments, the objective lens assembly 20 is configured for telecentric scanning of the electromagnetic radiation beam and the calibration plate 402 is supported to be perpendicular to the direction of propagation of the electromagnetic radiation beam. The calibration plate 402 is disposed between the objective lens assembly 20 and a light source 406. The light source 406 is used to illuminate the calibration plate 402. A portion of the illumination light from the light source 406 passes through each of the through holes 404, thereby producing an illuminated location within the field of view of the camera 62 at each of the through holes 404. A light beam 408 from each of the through holes 404 passes through the objective lens assembly 20, through the video dichroic 66, an into the camera 62. In many embodiments, the camera 62 includes a sensor having an orthogonal array of pixels (e.g., in x and y directions where the corresponding z direction is in the direction of propagation of the electromagnetic radiation beam). In many embodiments, X and Y pixel values for each of the light beams 408 is used in conjunction with the known locations of the through holes 404 relative to the objective lens assembly 20 to determine the relationship between the camera X and Y pixel values and locations in the treatment space for dimensions transverse to the propagation direction of the electromagnetic radiation beam.

Figure 11:
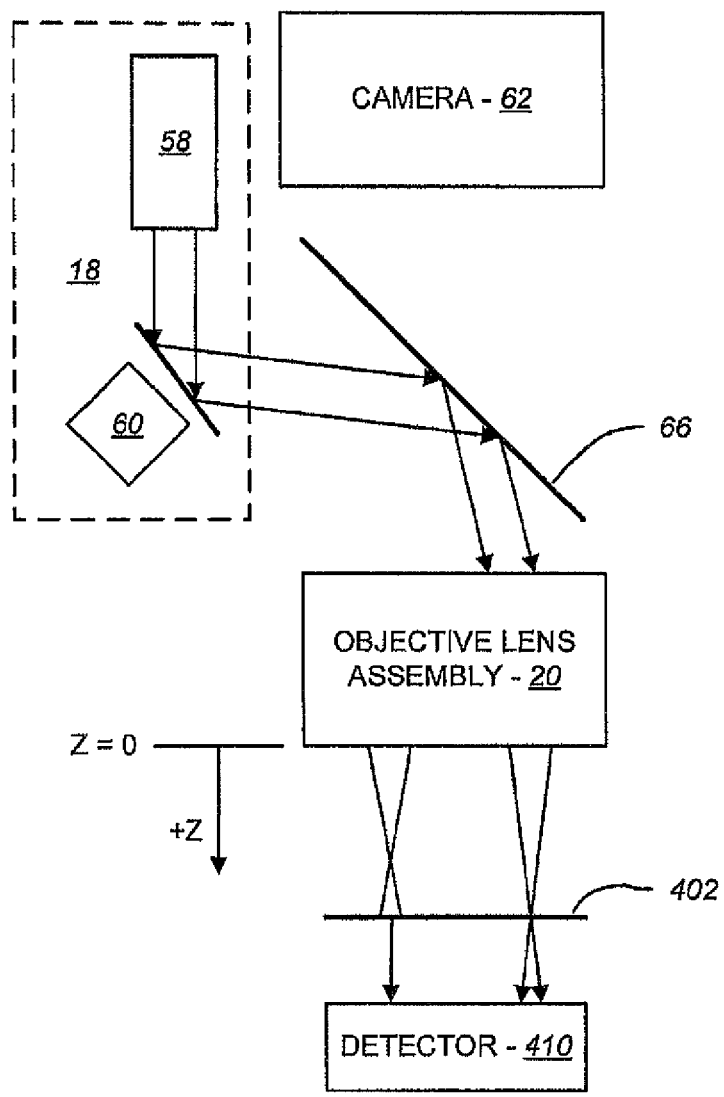
FIG. 11 is a schematic diagram illustrating using the calibration plate of FIG. 9 to calibrate the scanning assembly of the laser surgery system of FIG. 1.

FIG. 11 schematically illustrates using the calibration plate 402 to calibrate the scanning assembly 18. The calibration plate 402 is supported at a known fixed location relative to the objective lens assembly 20. In many embodiments, the objective lens assembly 20 is configured for telecentric scanning of the electromagnetic radiation beam and the calibration plate 402 is supported to be perpendicular to the direction of propagation of the electromagnetic radiation beam. The calibration plate 402 is disposed between the objective lens assembly 20 and a detector 410. The detector 410 is configured to generate a signal indicative of how much of the electromagnetic radiation beam is incident thereon, thereby being indirectly indicative of how much of the electromagnetic radiation beam is blocked by the calibration plate 402. For example, when the focal point of the electromagnetic radiation beam is positioned at one of the through holes 404 (as illustrated for the focal point disposed on the right side of the detection plate 402 in FIG. 11), a maximum amount of the electromagnetic radiation beam passes through the through hole and is incident on the detector 410. In contrast, when the focal point of the electromagnetic radiation beam is not positioned at one of the through holes 404 (as illustrated for the focal point disposed above the left side of the detection plate 402 in FIG. 11), a portion of the electromagnetic radiation beam is blocked from reaching the detector 410.

Control parameters for the z-scan device 58 and the xy-scan device 60 are varied to locate the focal point of the electromagnetic radiation beam at each of a suitable set of the through holes, thereby providing data used to determine the relationship between the control parameters for the scanning assembly 18 and the resulting location of the focal point of the electromagnetic radiation beam. The z-scan device 58 is operable to vary a convergence/divergence angle of the electromagnetic radiation beam, thereby being operable to control the distance of the focal point from the objective lens in the direction of propagation of the electromagnetic radiation beam. The xy-scan device 60 is operable to vary a direction of the electromagnetic radiation beam in two dimensions, thereby providing the ability to move the focal point in two dimensions transverse to the direction of propagation of the electromagnetic radiation beam.

A suitable existing search algorithm can be employed to vary the control parameters for the z-scan device 58 and the xy-scan device 60 so as to reposition the focal point to be located at each of a suitable set of the through holes 404. In many embodiments where the objective lens assembly 20 is configured to telecentrically scan the electromagnetic radiation beam, the resulting control parameter data for the scanning assembly 18 can be used to calibrate the scanning assembly 18 relative to directions transverse to the direction of propagation of the electromagnetic radiation beam (e.g., x and y directions transverse to a z direction of propagation of the electromagnetic radiation beam).

Figure 12:
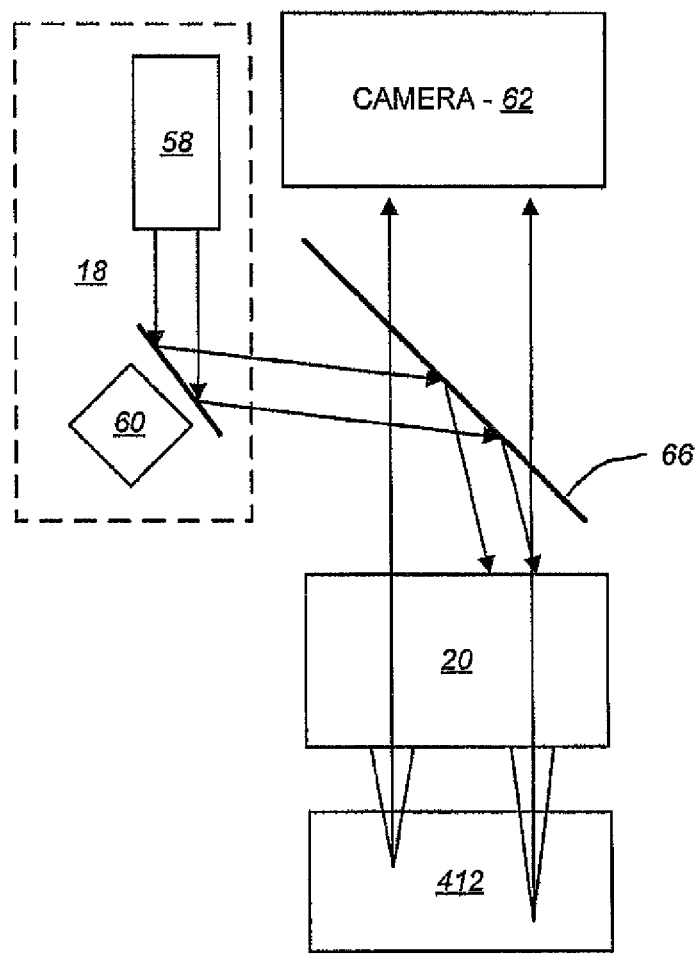
FIG. 12 is a schematic diagram illustrating using a fluorescent material to calibrate the scanning assembly of the laser surgery system of FIG. 1.

FIG. 12 schematically illustrates using a fluorescent material block 412 to calibrate the scanning assembly 18. The fluorescent material block 412 is made of a suitable fluorescent material that emits light in response to absorbing electromagnetic radiation. The fluorescent material block 412 is supported at a fixed location relative to the objective lens assembly 20. With the focal point of the electromagnetic radiation beam disposed within the block 412, the camera 62 is used to observe the location of the resulting fluorescent emission in the block 412. The observed location of the resulting fluorescent emission can be used in conjunction with calibration data for the camera 62 to determine x and y coordinates of the associated focal point in the treatment space. Suitable variation in the location of the focal point within the fluorescent material block 412 and associated position data for the resulting fluorescent emissions generated via the camera 62 can be used to calibrate the control parameters for the scanning assembly 18. For example, in embodiments where the objective lens assembly 20 is configured to telecentrically scan the focal point, the corresponding positional data for the resulting fluorescent emissions can be used to generate calibrated control parameters for the xy-scan device 60 for positioning the focal point transverse to the direction of propagation of the electromagnetic radiation beam.

Figure 13:
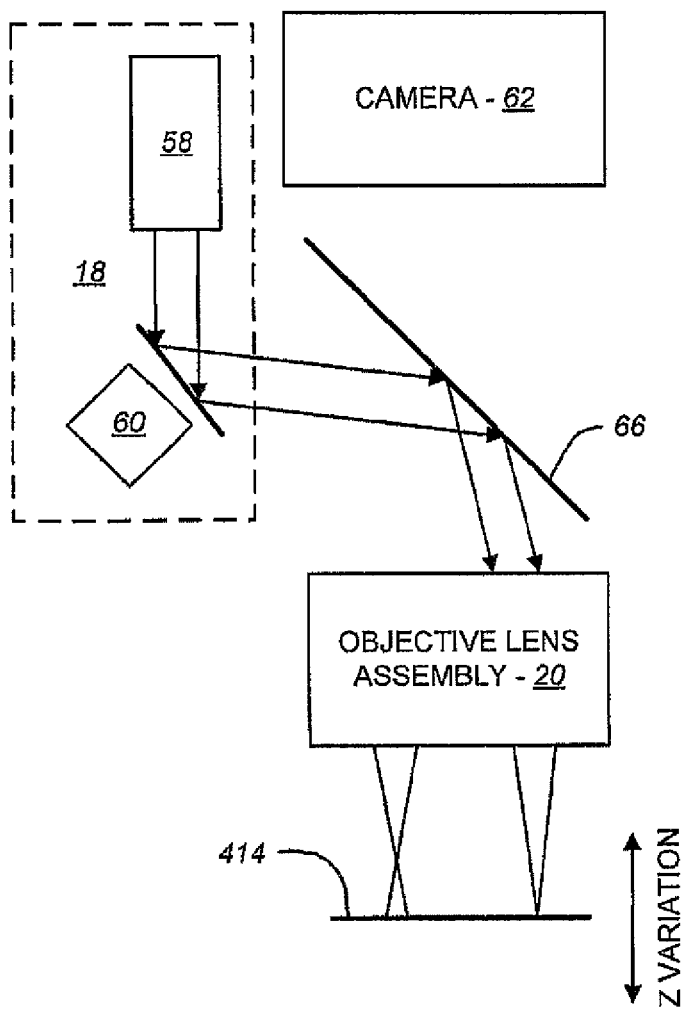
FIG. 13 is a schematic diagram illustrating using a repositionable reflective surface to calibrate the scanning assembly of the laser surgery system of FIG. 1.
Figure 14:
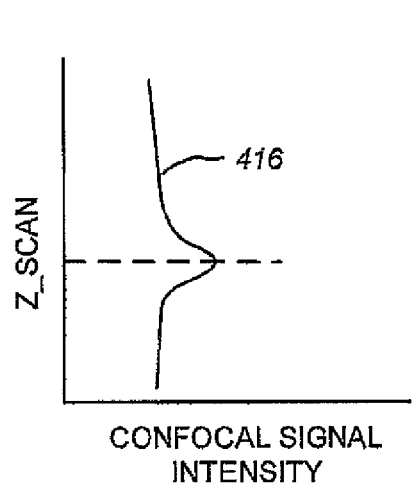
FIG. 14 illustrates variation in intensity of a signal generated using the reflective surface of FIG. 13 relative to a control parameter for a z-scan device of the laser surgery system of FIG. 1.

FIG. 13 schematically illustrates the use of a reflective member 414 to calibrate the scanning assembly 18. The reflective member 414 is supported at a suitable plurality of known fixed distances relative to the objective lens assembly 20. In many embodiments, the objective lens assembly 20 is configured for telecentric scanning of the electromagnetic radiation beam and the reflective member 414 is supported to be perpendicular to the direction of propagation of the electromagnetic radiation beam. The reflective member 414 reflects the electromagnetic radiation beam back through the objective lens assembly 20, back through the scanning assembly 18, back through the free-floating mechanism 16, and back to the confocal detection assembly 14. For a particular distance between the objective lens assembly 20 and the reflective member 414, the z-scan device 58 can be operated to vary the distance of the focal point from objective lens assembly. Alternatively, for a particular setting of the z-scan device resulting in a particular distance of the focal point from the objective lens assembly, the distance between the objective lens assembly 20 and the reflective member 414 can be varied. As illustrated in FIG. 14, a resulting signal 416 produced by the detection sensor 54 of the confocal detection assembly 14 varies in intensity with variation in the distance between the focal point and the reflective member 414. The intensity of the signal 416 generated by the detection sensor 54 is maximized when the focal point is located at the surface of the reflective member 414, thereby maximizing the amount of reflected light that passes through the pinhole aperture 52 to reach the detection sensor 54. By determining the values of the control parameter for the z-scan device 58 corresponding to a suitable plurality of distances between the reflective member 414 and the objective lens assembly 20, suitable calibration parameters can be generated for use in controlling the z-scan device 58 to control the location of the focal point in the treatment space in the direction of propagation of the electromagnetic radiation beam.

Focal Point Scan Control

Figure 15:
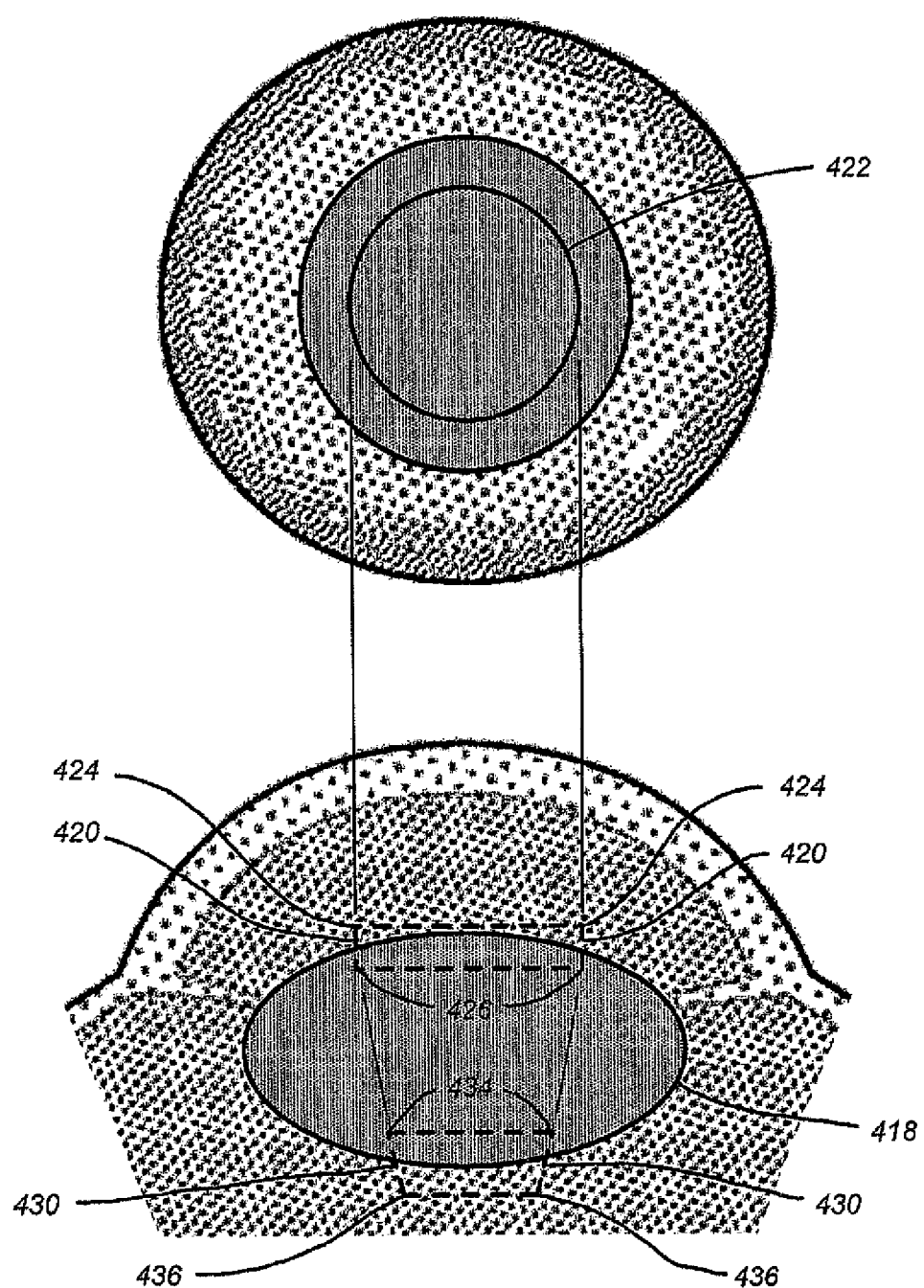
FIG. 15 shows a plan view of a capsulotomy incision locator and a cross-sectional view showing projection of the capsulotomy incision locator on the lens anterior capsule, in accordance with many embodiments.
Figure 16:
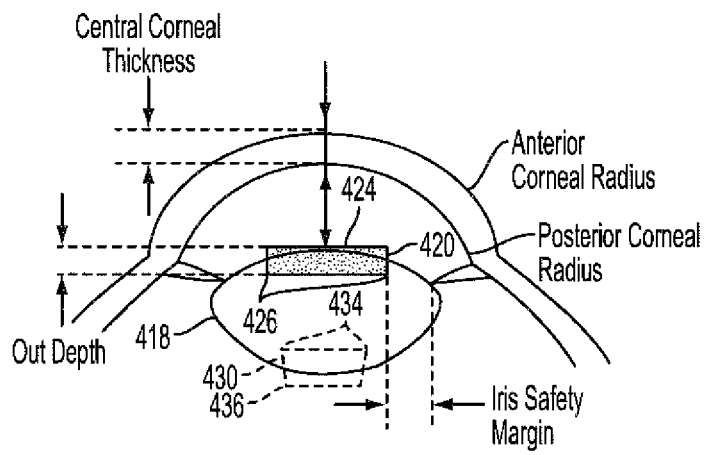
FIG. 16 shows a cross-sectional view of an eye and a capsulotomy incision region defining a closed boundary incision surface transecting the lens anterior capsule, in accordance with many embodiments.

The laser surgery system 10 can be configured to image and/or modify an intraocular target by scanning the focal point of the electromagnetic radiation beam in a particular area. For example, referring now to FIG. 15 and FIG. 16, the laser surgery system 10 can be used to incise an anterior capsulotomy and/or a posterior capsulotomy in the anterior portion of a lens capsule 418. The focal point of the electromagnetic radiation beam can be scanned to form an anterior capsulotomy closed incision boundary surface 420 that transects the anterior portion of the lens capsule 418. Likewise, the focal point of the electromagnetic radiation beam can be scanned to form a posterior capsulotomy closed incision boundary surface 430 that transects the posterior portion of the lens capsule 418.

The anterior and/or posterior closed incision boundary surfaces 420, 430 can be designated using any suitable approach. For example, a plan view of the patient's eye can be obtained using the camera 62. A capsulotomy incision designator 422 can be located and shown superimposed on the plan view of the patient's eye to illustrate the size, location, and shape of a planned capsulotomy relative to the patient's eye. The capsulotomy incision designator 422 can be manually defined by an operator of the laser surgery system 10 and/or the laser surgery system 10 can be configured to generate an initial capsulotomy incision designator 422 for operator verification and/or modification.

Figure 18:
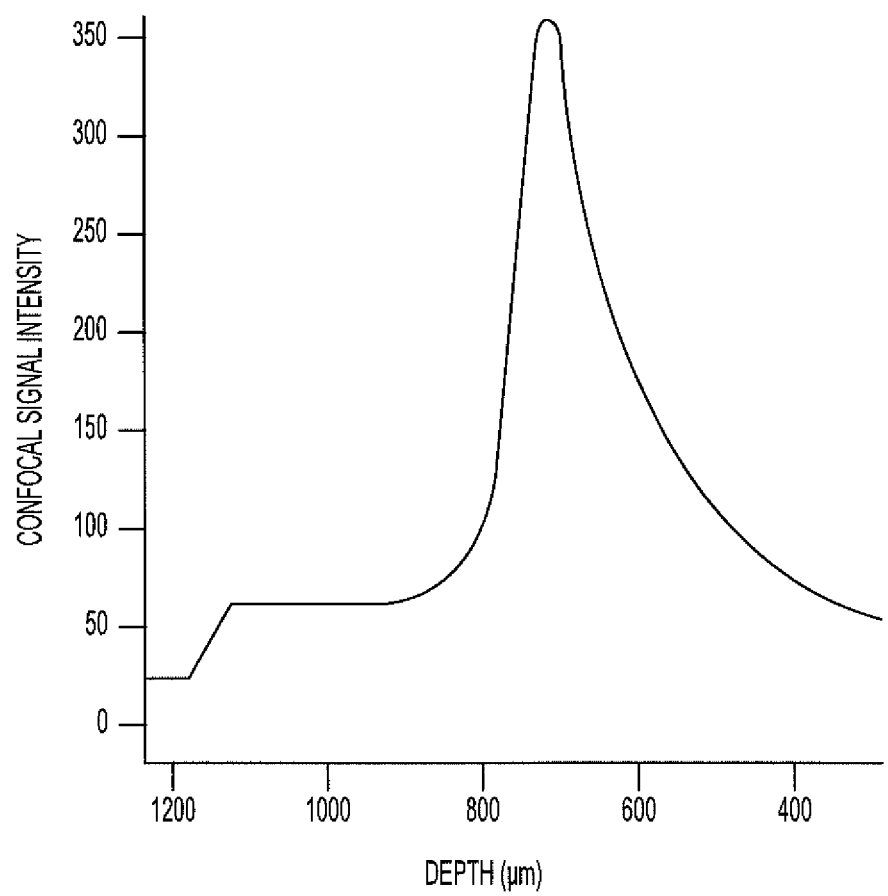
FIG. 18 illustrates variation in intensity of a signal generated while scanning the focal point of the electromagnetic radiation beam in a scan pattern that crosses a boundary of an intraocular target, in accordance with many embodiments.

The anterior capsulotomy closed incision boundary surface 420 can be defined on a projection of the capsulotomy incision designator 422 such that the anterior capsulotomy closed incision boundary surface 420 transects the anterior portion of the lens capsule 418 at all locations around the anterior capsulotomy incision boundary surface 420 for all expected variations in the location of the anterior portion of the lens capsule 418 relative to the projection of the capsulotomy incision designator 422. For example, a curve corresponding to the capsulotomy incision designator 422 can be projected to define an intersection with a minimum depth mathematical surface model (e.g., a spherical surface) defining a minimum expected depth configuration for the anterior portion of the lens capsule 418 with the resulting intersection being an anterior capsulotomy upper closed curve 424 that defines an upper boundary for the anterior capsulotomy closed incision boundary surface 420. Likewise, the curve corresponding to the capsulotomy incision designator 422 can be projected to define an intersection with a maximum depth mathematical surface model (e.g., a spherical surface) defining a maximum expected depth configuration for the anterior portion of the lens capsule 418 with the resulting intersection being an anterior capsulotomy lower closed curve 426 that defines a lower boundary for the anterior capsulotomy closed incision boundary surface 420. Alternatively, the focal point can be scanned using a low imaging-only power level (e.g., a power level sufficient to provide for imaging of the intraocular target via processing of the signal generated by the detection sensor 54 of the confocal detection assembly 14 without modifying the intraocular target) along the projection of the capsulotomy incision designator 422 while varying the depth of the focal point to determine the depth of the anterior lens capsule at a sufficient number of locations around the projection of the capsulotomy incision designator 422. For example, FIG. 18 illustrates variation of intensity of the signal generated by the detection sensor 54 with variation in depth of the focal point with the maximum peak in intensity corresponding to the depth of the anterior portion of the lens capsule 418. The measured depths of the anterior lens capsule can then be used to determine suitable anterior capsulotomy upper and lower boundary curves 424, 426 of the anterior capsulotomy closed incision boundary surface 420.

In a similar fashion, the posterior capsulotomy closed incision boundary surface 430 can be defined on a projection of the capsulotomy incision designator 422 such that the posterior capsulotomy closed incision boundary surface 430 transects the posterior portion of the lens capsule 418 at all locations around the posterior capsulotomy incision boundary surface 430 for all expected variations in the location of the posterior portion of the lens capsule 418 relative to the projection of the capsulotomy incision designator 422. For example, the curve corresponding to the capsulotomy incision designator 422 can be projected to define an intersection with a minimum depth mathematical surface model (e.g., a spherical surface) defining a minimum expected depth configuration for the posterior portion of the lens capsule 418 with the resulting intersection being a posterior capsulotomy upper closed curve 434 that defines an upper boundary for the posterior capsulotomy closed incision boundary surface 430. Likewise, the curve corresponding to the capsulotomy incision designator 422 can be projected to define an intersection with a maximum depth mathematical surface model (e.g., a spherical surface) defining a maximum expected depth configuration for the posterior portion of the lens capsule 418 with the resulting intersection being a posterior capsulotomy lower closed curve 436 that defines a lower boundary for the posterior capsulotomy closed incision boundary surface 430. Alternatively, the focal point can be scanned using a low imaging-only power level (e.g., a power level sufficient to provide for imaging of the intraocular target via processing of the signal generated by the detection sensor 54 of the confocal detection assembly 14 without modifying the intraocular target) along the projection of the capsulotomy incision designator 422 while varying the depth of the focal point to determine the depth of the posterior lens capsule at a sufficient number of locations around the projection of the capsulotomy incision designator 422. The measured depths of the posterior lens capsule can then be used to determine suitable posterior capsulotomy upper and lower boundary curves 434, 436 of the posterior capsulotomy closed incision boundary surface 430.

While any suitable projection of the capsulotomy incision designator 422 can be used to define the anterior and/or posterior capsulotomy incision boundary surfaces 420, 430, in many embodiments an inverted cone shaped projection of the capsulotomy incision designator 422 is employed so as to maintain a suitable safety margin distance between the electromagnetic radiation beam, which converges to the focal point while propagating from the objective lens assembly 20 to the focal point, and the edge of the iris. Accordingly, in many embodiments, the posterior capsulotomy has a smaller diameter than a corresponding anterior capsulotomy for a given capsulotomy incision designator 422, for example, as illustrated.

The laser surgery system 10 can be used to form any suitably shaped capsulotomy. For example, while the anterior and posterior capsulotomies in the illustrated embodiments are circular, any other suitable shape, including but not limited to, elliptical, rectangular, and polygonal can be formed. And the anterior and/or posterior capsulotomy can be shaped to accommodate any correspondingly suitably shaped IOL.

Concurrent Imaging and Adaptive Tissue Treatment

The laser surgery system 10 can be configured to generate image data concurrent with tissue treatment. For example, the focal point of the electromagnetic radiation beam can have an intensity sufficient to modify an intraocular target (e.g., eye tissue, an IOL) with a resulting portion of the electromagnetic radiation beam reflected from the focal point back to the detection sensor 54 of confocal detection assembly 14 used to generate a signal that is processed to generate image data corresponding to the focal point location.

By scanning the focal point in a pattern that crosses a boundary of an intraocular target, the detection sensor 54 can be used to concurrently generate a signal that can be processed to identify the location of the crossed boundary. For example, FIG. 18 illustrates variation of intensity of the signal generated by the detection sensor 54 with variation in depth of the focal point with the maximum peak in intensity corresponding to the depth of the anterior portion of the lens capsule 418. The location of the crossed boundary can be used to control subsequent scanning of the focal point so as to reduce the amount of tissue that is treated. For example, when incising an anterior capsulotomy in the lens capsule, the focal point can be scanned in a scan pattern that is at least in part based on the location of the anterior portion of the lens capsule as determined by processing the signal from the detection sensor 54 generated during a previous scan pattern.

Figure 17:
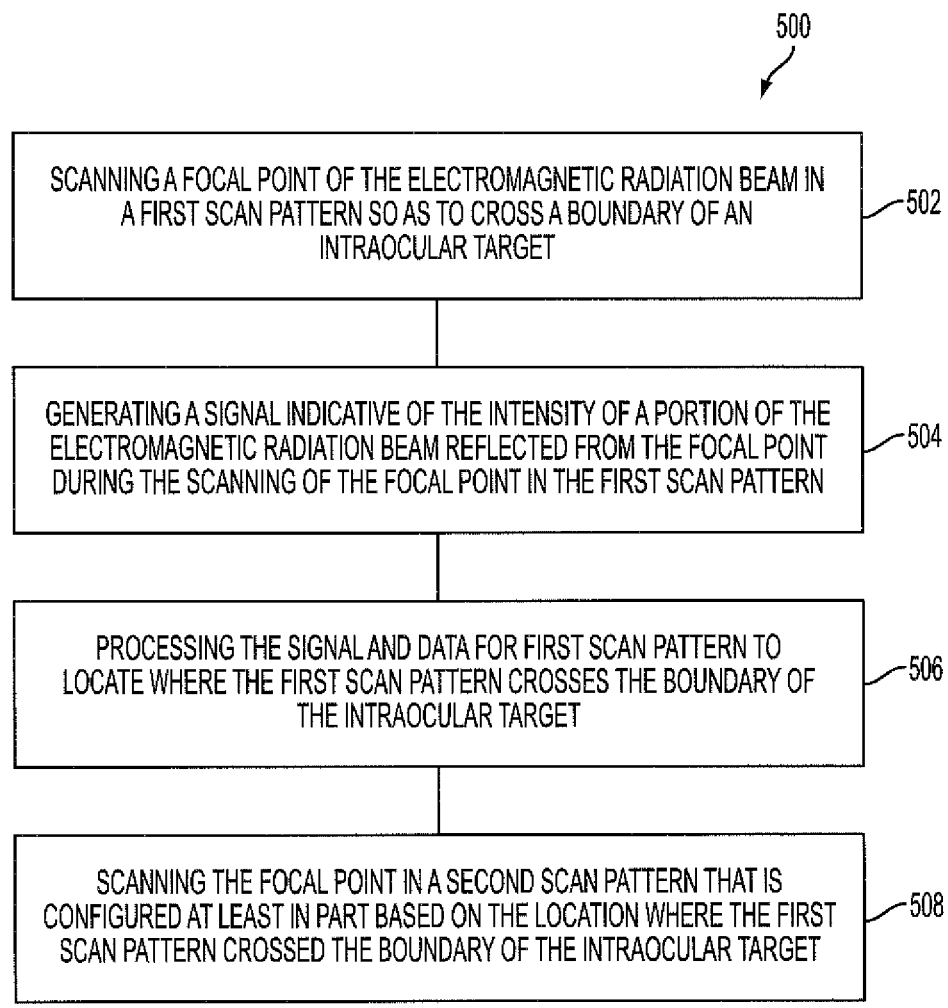
FIG. 17 is a simplified block diagram of acts of a method for adaptively scanning the focal point of the electromagnetic radiation beam relative to a boundary of an intraocular target, in accordance with many embodiments.

FIG. 17 is a simplified block diagram of acts of a method 500 for adaptively scanning the focal point of the electronic radiation beam relative to a boundary of an intraocular target, in accordance with many embodiments. The method 500 can be accomplished, for example, using any suitable system including any suitable laser surgery system described herein such as the laser surgery system 10.

The method 500 includes scanning a focal point of the electromagnetic radiation beam in a first scan pattern so as to cross a boundary of an intraocular target (act 502). In many embodiments, the scan pattern moves the focal point transverse to and/or parallel to the direction of propagation of the electromagnetic radiation beam. The intraocular target having the crossed boundary can be any suitable intraocular target including, for example, the anterior lens capsule, the posterior lens capsule, the crystalline lens, the cornea, the iris, an intraocular lens, and the limbus. Where a plurality of scan patterns is applied to create an incision surface (e.g., the closed incision boundary surface 420 shown in FIGS. 15 and 16), the scan patterns can be configured such that the electromagnetic radiation beam propagates to the focal point through unmodified eye tissue and/or IOL material. For example, the scan patterns can be configured and accomplished such that modification occurs in a generally deeper to shallower manner.

The method 500 further includes generating a signal indicative of the intensity of a portion of the electromagnetic radiation beam reflected from the focal point during the scanning of the focal point in the first scan pattern (act 504). For example, because the first scan pattern crosses the boundary of the intraocular target, the signal generated by the detection sensor (e.g., such as the signal illustrated in FIG. 18) and focal point position data for the first scan pattern can be processed to determine the location of the crossed boundary (act 506) by, for example, identifying a signal variation consistent with the applicable boundary.

Having determined the location of where the first scan pattern crossed the boundary of the intraocular target, the focal point can be scanned in a second scan pattern that is configured at least in part based on the location where the first scan pattern crossed the boundary of the intraocular target (act 508). For example, the second scan pattern can be configured to only extend beyond an estimated location of where the second scan pattern will cross the boundary of the intraocular target by predetermined amounts selected to account for possible variations in the estimated location of where the second scan pattern will cross the boundary in view of knowing where the first scan pattern crossed the boundary of the intraocular target. In many embodiments, the second scan pattern will be immediately adjacent to if not overlapped with the first scan pattern, thereby reducing the possible variation between the measured location where the first scan pattern crossed the boundary and the estimated location where the second scan pattern will cross the boundary. In many embodiments in which an incision surface is created, a series of subsequent scan patterns can be accomplished in which the location where one or more previous scan patterns crossed the boundary of the intraocular lens can be used to configured at least one of the subsequent scan patterns to, for example, minimize the tissue and/or material modified and/or increase the accuracy with regard to which tissue and/or material is modified.

Figure 19:
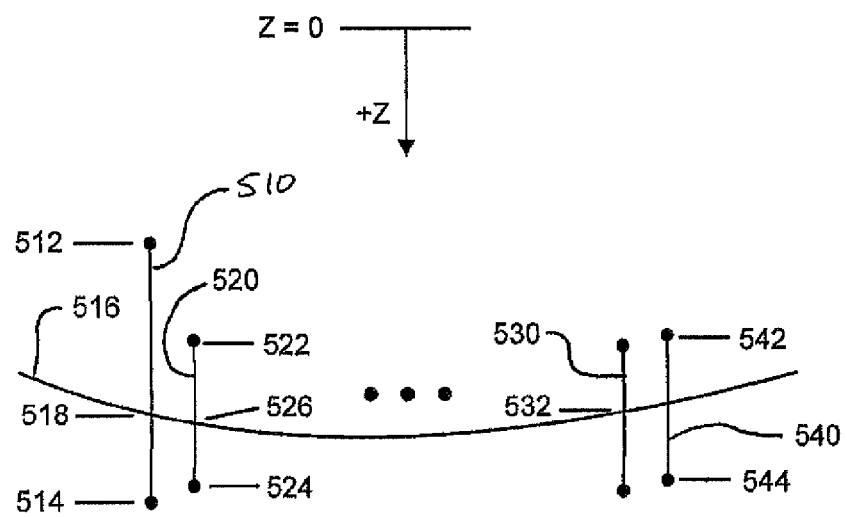
FIG. 19 is a schematic diagram illustrating repeatedly using a location of where a scan pattern for the focal point crosses a boundary of an intraocular target to determine upper and/or lower depth limits for a subsequent scan pattern for the focal point, in accordance with many embodiments.

FIG. 19 schematically illustrates repeated use of a location where a scan pattern for the focal point crossed a boundary of an intraocular target to configure a subsequent scan pattern. While FIG. 19 employs scan patterns having variation in the location of the focal point relative to the z-dimension (i.e., parallel to the direction of propagation of the electromagnetic radiation beam), the concept illustrated can be adapted to apply to any suitable scan pattern having, for example, variation in the location of the focal point relative to directions transverse to as well as transverse to and parallel to the direction of propagation of the electromagnetic radiation beam (e.g., x-direction variation, y-direction variation, and/or z-direction variation). An initial scan pattern 510 can be configured so as to extend between two locations 512, 514 that are selected so that the initial scan pattern 510 crosses a boundary 516 for an intraocular target for all expected variations in the location of the boundary 516. By processing the signal generated by the detection sensor 54 during the initial scan pattern 510 along with focal point location data for the initial scan pattern 510, a location 518 where the initial scan pattern 510 crossed the boundary 516 can be identified.

A second scan pattern 520 can then be configured at least in part based on the location 518. For example, end locations 522, 524 for the second scan pattern 520 can be selected based on the location 518 so as to, for example, substantially minimize the length of the second scan pattern so as to minimize the amount of tissue and/or material treated. By processing the signal generated by the detection sensor 54 during the second scan pattern 520 along with focal point location data for the second scan pattern 520, a location 526 where the second scan pattern 520 crossed the boundary 516 can be identified.

Any suitable subsequent scan pattern can be configured in a similar fashion. For example, by processing the signal generated by the detection sensor during a scan pattern 530 along with focal point location data for the scan pattern 530, a location 532 where the scan pattern 530 crossed the boundary 516 can be identified. End points 542, 544 for a subsequent scan pattern 540 can be selected based on the location 532 so as to, for example, substantially minimize the length of the scan pattern 540 so as to minimize the amount of tissue and/or material treated. Accordingly, a series of scan patterns can be adaptively configured and applied using boundary location data for the intraocular target generated from one or more previous scan patterns.

Figure 20:
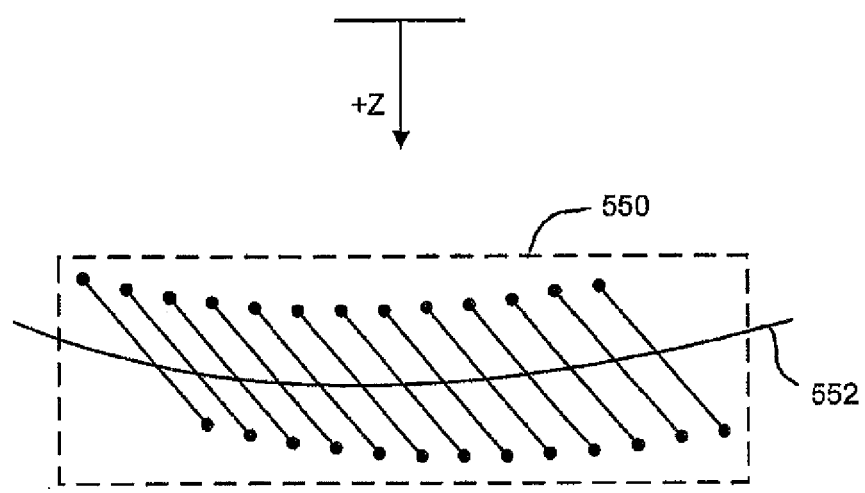
FIG. 20 is a schematic diagram illustrating a series of scan patterns that can be used to incise a surface that transects a boundary of an intraocular target, in accordance with many embodiments.

FIG. 20 illustrates a series of scan patterns 550 that can be used to incise a surface that transects a boundary 552 of an intraocular target. In the illustrated embodiment, the scan patterns 550 are adaptively configured using boundary location data generated from one or more previous scan patterns of the series of scan patterns 550, such as described above with respect to FIG. 19 and method 500. Accordingly, the series of scan patterns 550 can be configured to generally extend beyond both sides of the boundary 552 by substantially uniform distances and thereby follow the general shape of the boundary 552.

Figure 21:
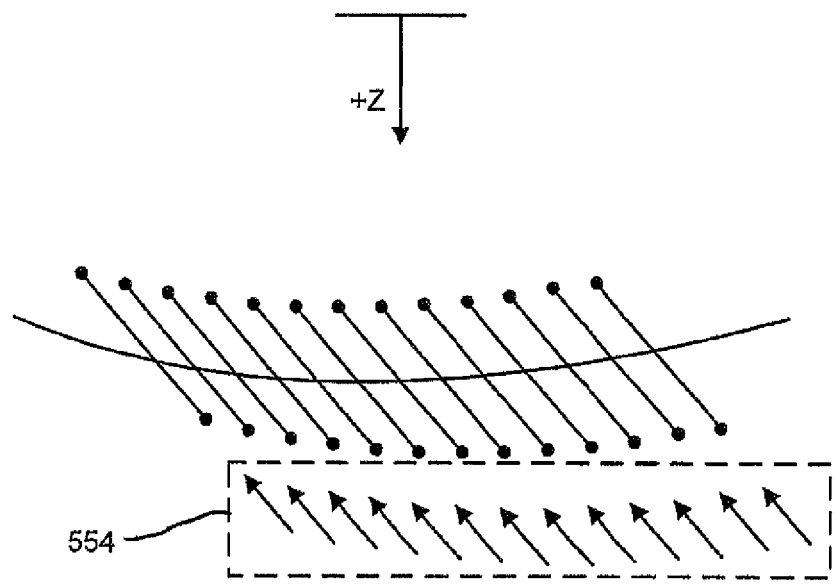
FIG. 21 and FIG. 22 are schematic diagrams illustrating embodiments of scanning directions that can be used with the scan patterns of FIG. 20.
Figure 22:
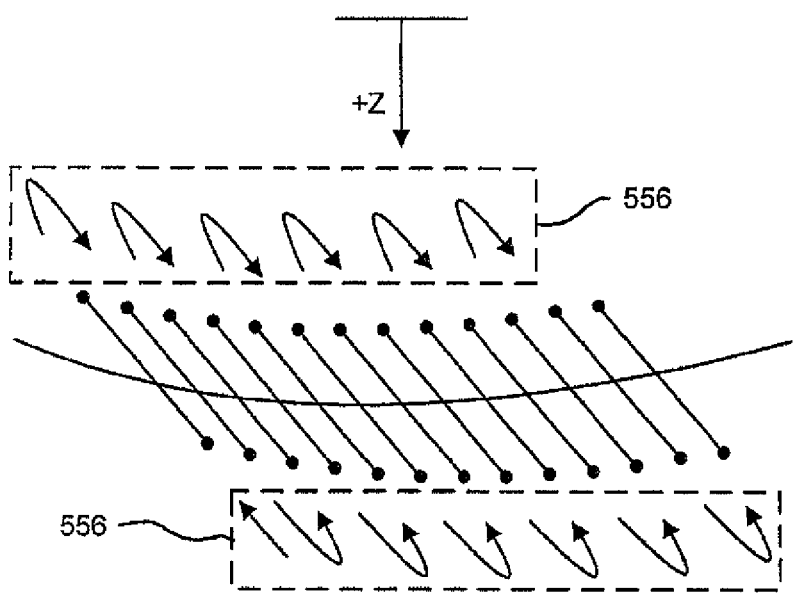

FIGS. 21 and 22 illustrate scanning directions 554, 556 that can be used to incise the series of scan patterns 550. While any suitable scanning directions can be used, the illustrated directions 554, 556 can be used to avoid having the electromagnetic radiation beam propagate through previously treated tissue/material prior to reaching the focal point.

Corneal Incisions

The laser surgery system 10 can be configured to create different types of corneal incisions including, for example, one or more arcuate (e.g., relaxation) incisions, one or more cataract surgery primary access incisions, and/or one or more cataract surgery secondary (sideport) incisions. Each of these types of corneal incisions can be made in one or more different configurations.

Figure 23:
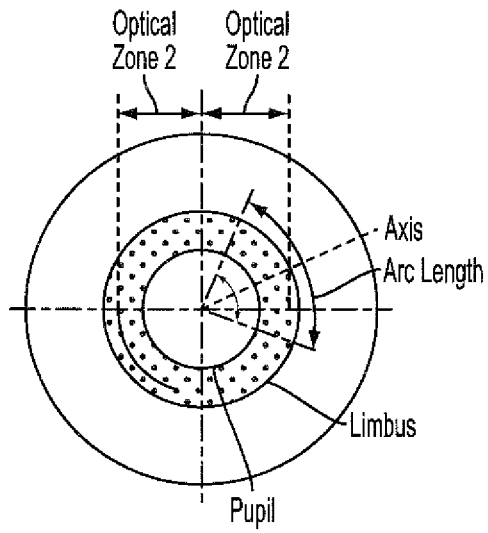
FIGS. 23 through 25 illustrate aspects of arcuate incisions of a cornea that can be formed by the laser surgery system of FIG. 1, in accordance with many embodiments.
Figure 24:
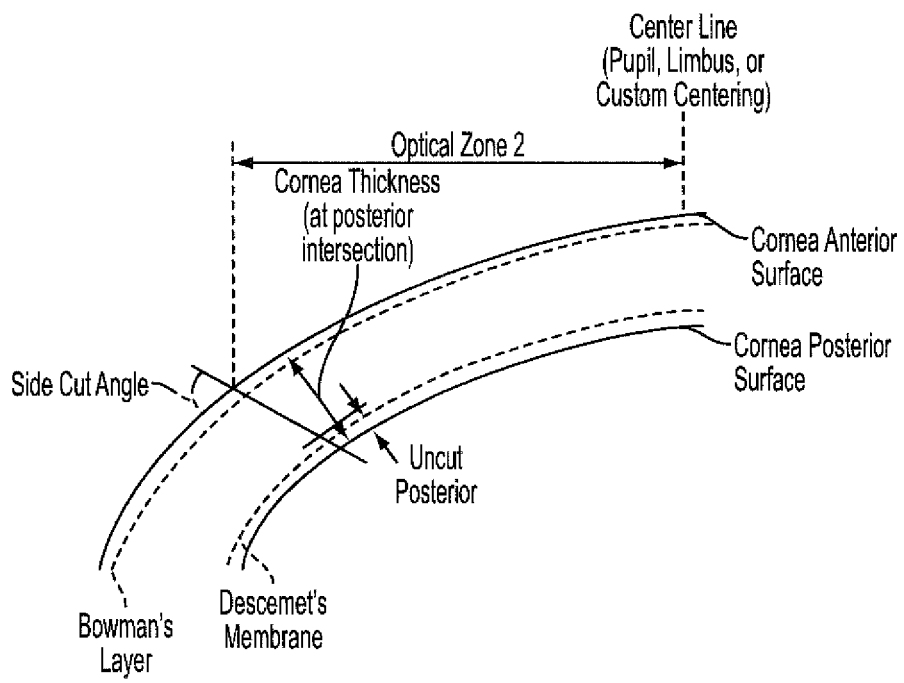
Figure 25:
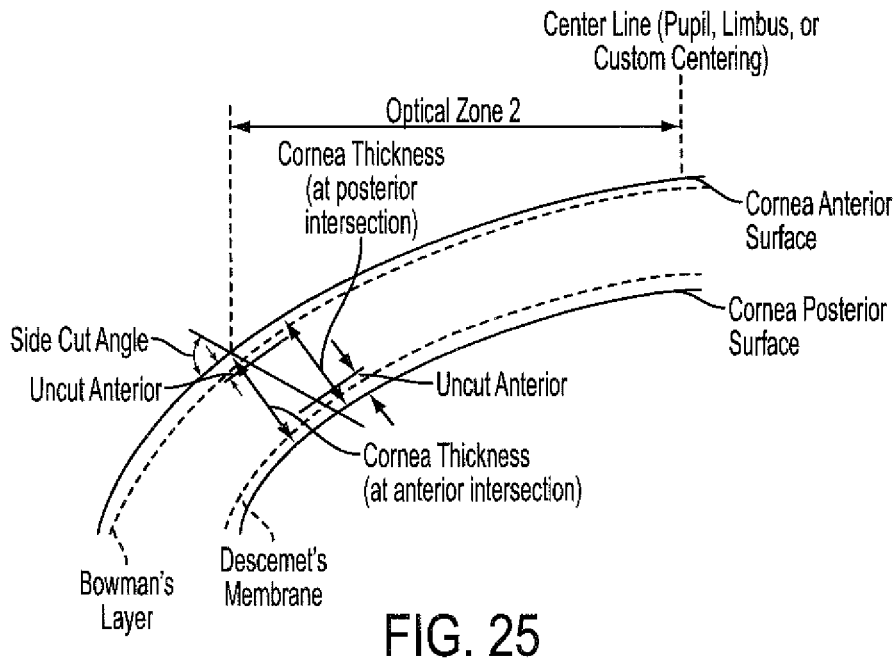

FIGS. 23 through 25 illustrate aspects of arcuate incisions of a cornea that can be formed by the laser surgery system 10, in accordance with many embodiments. FIG. 23 shows an en face view of arcuate incisions within the optical zone of the cornea that can be formed using the laser surgery system 10. The optical zone can user-adjustable within, for example, the range of 2 mm-11 mm. For asymmetric arcuate incisions, the optical zone can be independently adjustable for each incision. Arc length can be user-adjustable within, for example, the range of 10°-120°.

FIG. 24 shows a cross-sectional view of an arcuate incision in the cornea that can be formed using the laser surgery system 10 and that penetrates the cornea anterior surface and has an uncut posterior portion. FIG. 25 shows a cross-sectional view of an arcuate intrastromal incision in the cornea that can be formed using the laser surgery system 10. The arcuate intrastromal incision has an uncut anterior portion and an uncut posterior portion. Side cut angle can user-adjustable within, for example, the range of 30°-150°. Uncut posterior and anterior portions can be user-adjustable within, for example, the range of 100 µm-250 µm or 20%-50% of the cornea thickness. Cornea thickness can be measured at the projected intersection of the incision with the cornea anterior/posterior measured at 90° to anterior/posterior cornea surface regardless of what side cut angle is chosen.

Figure 26:
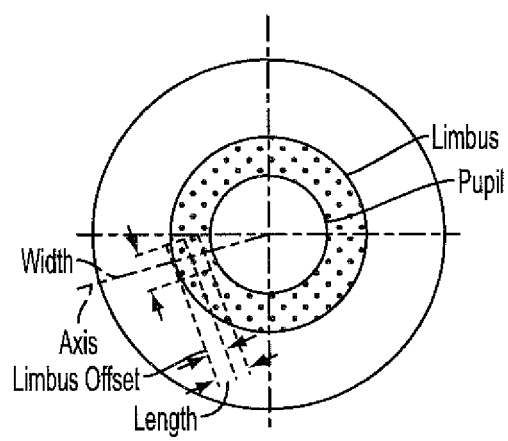
FIGS. 26 through 31 illustrate aspects of primary cataract surgery access incisions of a cornea that can be formed by the laser surgery system of FIG. 1, in accordance with many embodiments.
Figure 27:
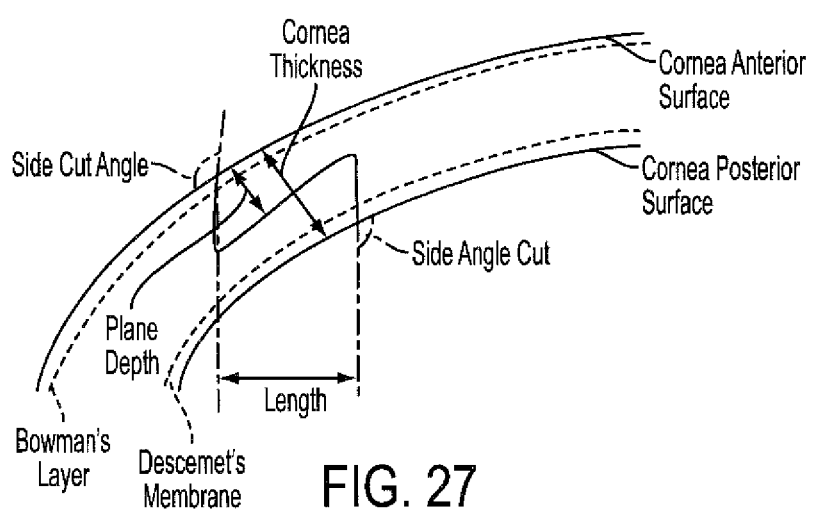
Figure 28:
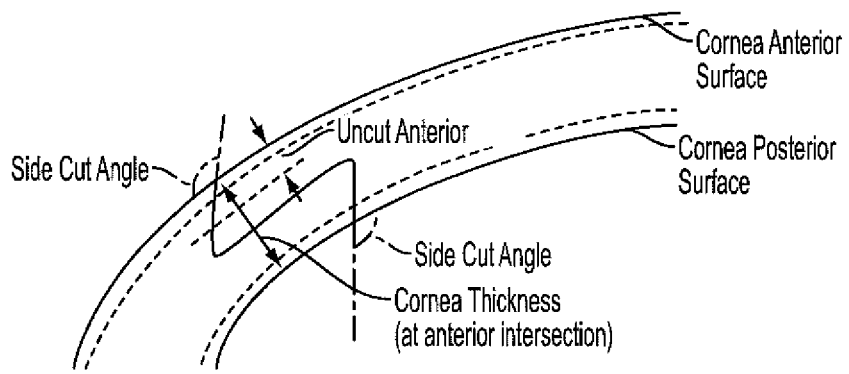
Figure 29:
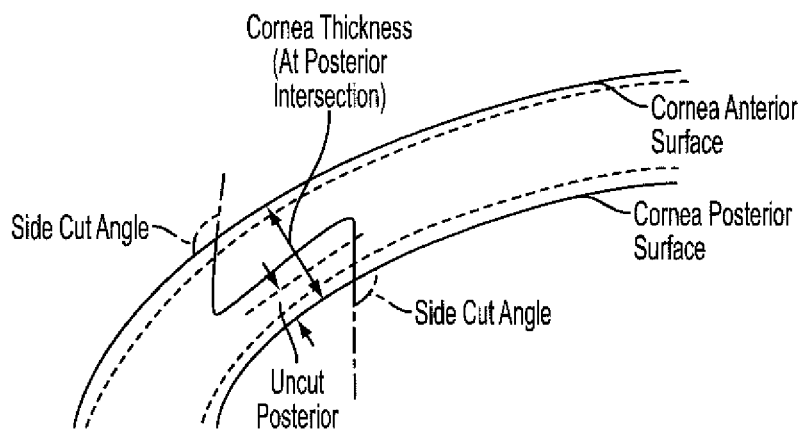
Figure 30:
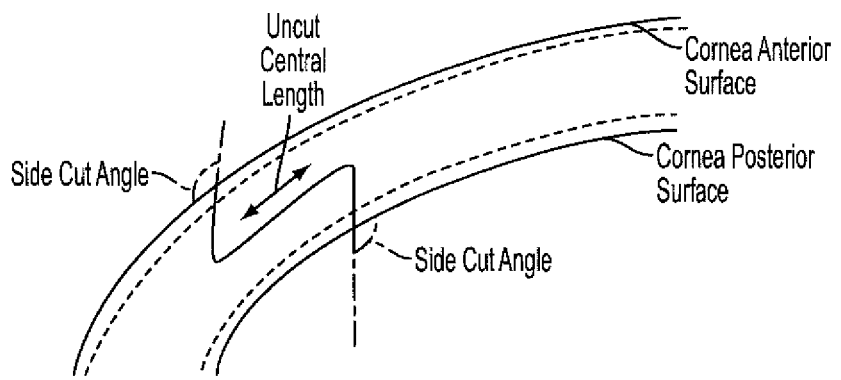
Figure 31:
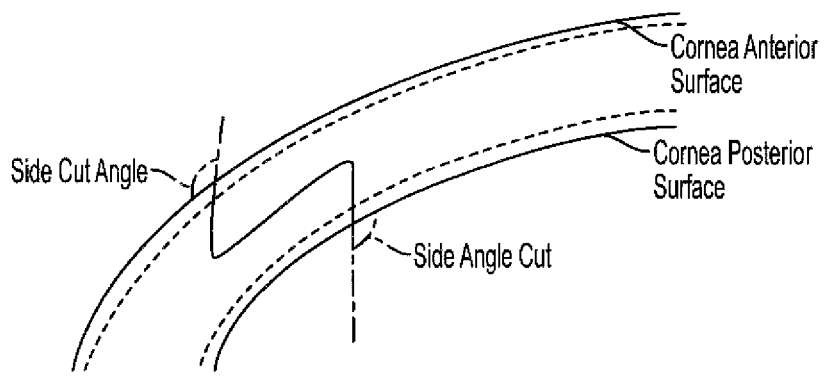

FIG. 26 shows an en face view of a primary cataract incision in the cornea that can be formed using the laser surgery system 10. The primary cataract incision provides access to surgical tools used to, for example, remove a fragmented crystalline lens nucleus and insert an IOL. FIG. 27 shows a cross-sectional view of a primary cataract incision of the cornea that can be formed using the laser surgery system 10. Limbus offset can be user-adjustable within, for example, the range of 0.0 mm-5.0 mm. Width can be user-adjustable within, for example, the range 0.2 mm-6.5 mm. Length can be user-adjustable within, for example, the range of 0.5 mm-3.0 mm. Side Cut Angle can be user-adjustable within, for example, the range of 30°-150°. Plane depth can be user-adjustable within, for example, the range of 125 µm-375 µm or 25%-75% of the cornea thickness. Length can be defined as the en face view distance between the projected incision intersection with the cornea anterior and the cornea posterior. FIG. 28 shows a cross-sectional view of a primary cataract incision that includes an uncut anterior portion. FIG. 29 shows a cross-sectional view of a primary cataract incision that includes an uncut posterior portion. FIG. 30 shows a cross-sectional view of a primary cataract incision that includes an uncut central length. And FIG. 31 shows a cross-sectional view of a primary cataract incision that includes no uncut portion. Side Cut Angle can be user-adjustable within, for example, the range of 30°-150°. Uncut central length can be user-adjustable within, for example, the range of 25 µm-1000 µm.

Figure 32:
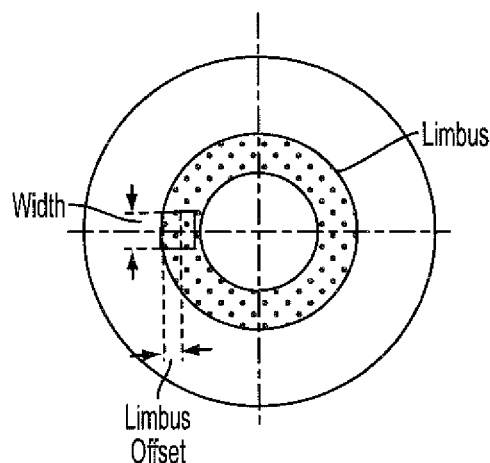
FIGS. 32 through 36 illustrate aspects of sideport cataract surgery access incisions of a cornea that can be formed by the laser surgery system of FIG. 1, in accordance with many embodiments.
Figure 33:
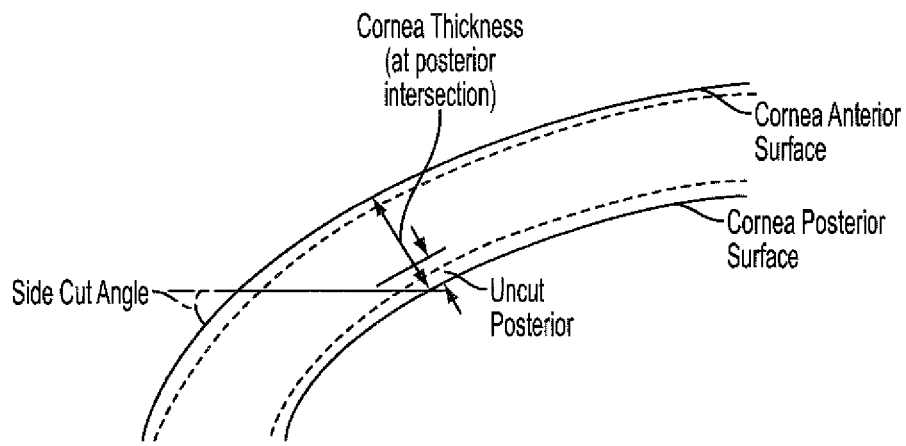
Figure 34:
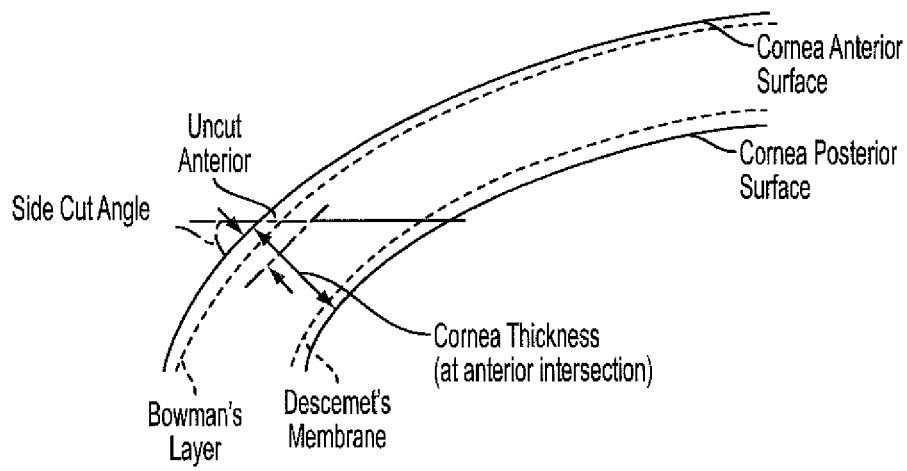
Figure 35:
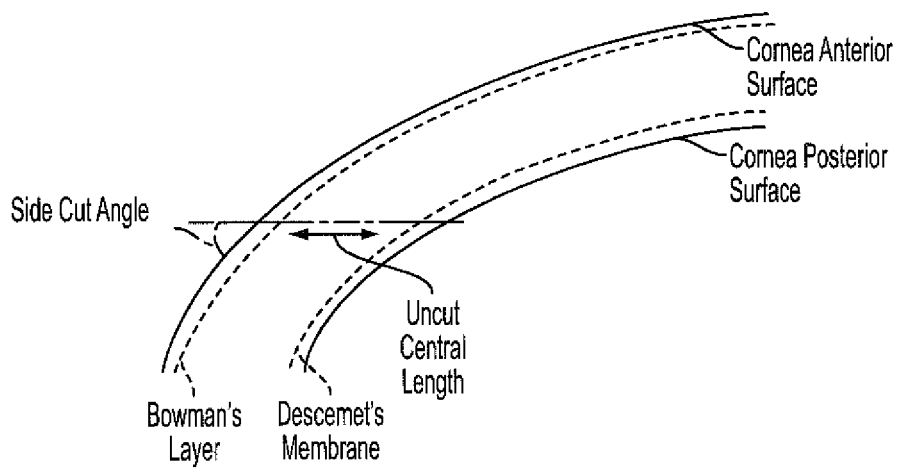
Figure 36:
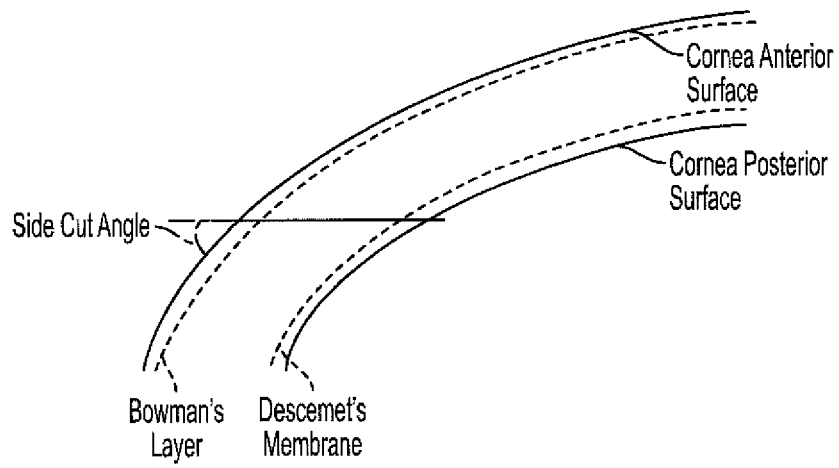

FIG. 32 shows an en face view of a sideport cataract incision in the cornea that can be formed using the laser surgery system 10. The sideport cataract incision provides access for surgical tools used, for example, to assist in the removal of a fragmented crystalline lens. FIG. 33 shows a cross-sectional view of a sideport cataract incision of the cornea that has an uncut posterior portion and can be formed using the laser surgery system 10. Limbus offset can be user-adjustable within, for example, the range of 0.0 mm-5.0 mm. Width can be user-adjustable within, for example, the range 0.2 mm-6.5 mm. Length can be user-adjustable within, for example, the range of 0.5 mm-3.0 mm. FIG. 34 shows a cross-sectional view of a sideport cataract incision that includes an uncut anterior portion. FIG. 35 shows a cross-sectional view of a sideport cataract incision that includes an uncut central length. And FIG. 36 shows a cross-sectional view of a sideport cataract incision that includes no uncut portion. Side Cut Angle can be user-adjustable within, for example, the range of 30°-150°. Uncut central length can be user-adjustable within, for example, the range of 100 µm-250 µm or 20%-50% of the cornea thickness. Cornea thickness can be measured at the projected intersection location of the incision with the cornea anterior/posterior measured at 90° to the anterior/posterior cornea surface regardless of what side cut angle is chosen.

Real-Time Monitoring Based Intensity Control

The laser surgery system 10 can be configured to use real-time monitoring to control the intensity of the electromagnetic radiation beam. The real-time monitoring can include, for example, monitoring of the signal generated by the detection sensor 54 of the confocal imaging assembly 14 and/or monitoring a sensor (e.g., a microphone) configured to detect specific target structures or the occurrence of a cavitation event.

Figures 37, 38:
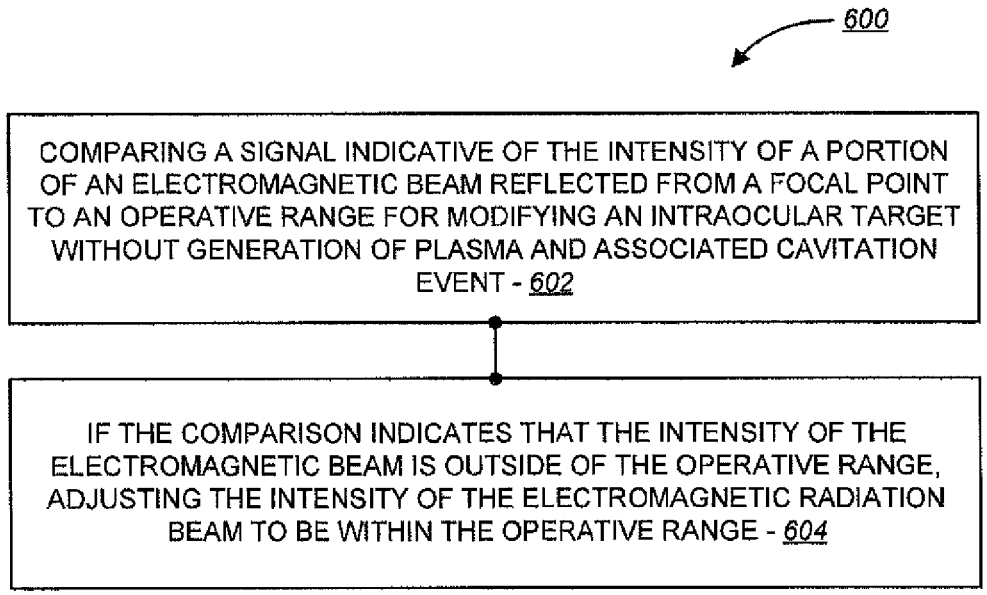
FIGS. 37 and 38 are simplified block diagrams of acts of methods for controlling the intensity of an electromagnetic radiation beam that can be used in the laser surgery system of FIG. 1, in accordance with many embodiments.

FIG. 37 is a simplified block diagram of acts of a method 600 for controlling the intensity of an electromagnetic radiation beam used to modify an intraocular target (e.g., tissue, IOL). The method 600 can be accomplished, for example, using any suitable system including any suitable laser surgery system described herein such as the laser surgery system 10.

The method 600 includes comparing a signal indicative of the intensity of a portion of an electromagnetic radiation beam reflected from a focal point to an operative range for modifying an intraocular tissue without generation of plasma and associated cavitation event (act 602). The signal can be generated, for example, by the detection sensor 54 of the laser surgery system 10. If the comparison indicates that the intensity of the electromagnetic beam is outside of the operative range (10 micro joules for example), the intensity of the electromagnetic radiation beam is adjusted to be within the operative range (act 604).

FIG. 38 is a simplified block diagram of acts of a method 610 for controlling the intensity of an electromagnetic radiation beam used to modify an intraocular target (e.g., tissue, IOL). The method 610 can be accomplished, for example, using any suitable system including any suitable laser surgery system described herein such as the laser surgery system 10.

The method 610 includes monitoring an intraocular target for an occurrence of a cavitation event generated by the electromagnetic radiation beam used to modify the intraocular target (act 612). For example, the signal generated by the detection sensor 54 of the laser surgery system 10 can be monitored for the occurrence of a cavitation event in the intraocular target. This would lead to an increased confocal signal reflection from the eye that may indicate an over treatment. In such a case, the laser pulse energy can be automatically reduced by the control electronics 304. The laser surgery system 10 can also incorporate a sensor (e.g., a microphone) configured to detect the occurrence of a cavitation event in the intraocular target. If an occurrence of a cavitation event in the intraocular target is detected, the intensity of the electromagnetic radiation beam is reduced (act 614).

Posterior Capsulotomy Through an IOL

In some instances, the posterior portion of a lens capsule of a patient's eye may become at least partially opaque subsequent to the installation of an intraocular lens (IOL). In such instances, it may be preferable to perform a posterior capsulotomy through the IOL to avoid removal of the IOL. In many embodiments, the laser surgery system 10 can be configured to perform a posterior capsulotomy through an IOL. For example, the laser surgery system 10 using an electromagnetic radiation beam having a wavelength between 320 nm to 430 nm can be used to perform a posterior capsulotomy through an IOL made from a material sufficiently transmissive of the wavelength used. While any suitable electromagnetic radiation beam of any suitable wavelength can be used, a wavelength between 320 nm to 430 nm can be used to maximize scattering of the electromagnetic radiation beam by the vitreous so as to minimize possible damage to the retina.

Figure 39:
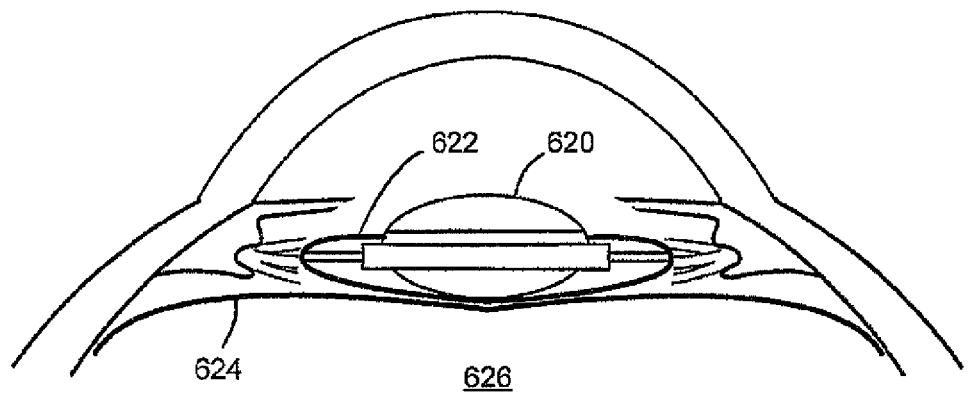
FIG. 39 is a side view diagram of an IOL positioned in a lens capsule and an adjacent portion of the anterior hyaloid surface of the vitreous, in accordance with many embodiments.
Figure 40:
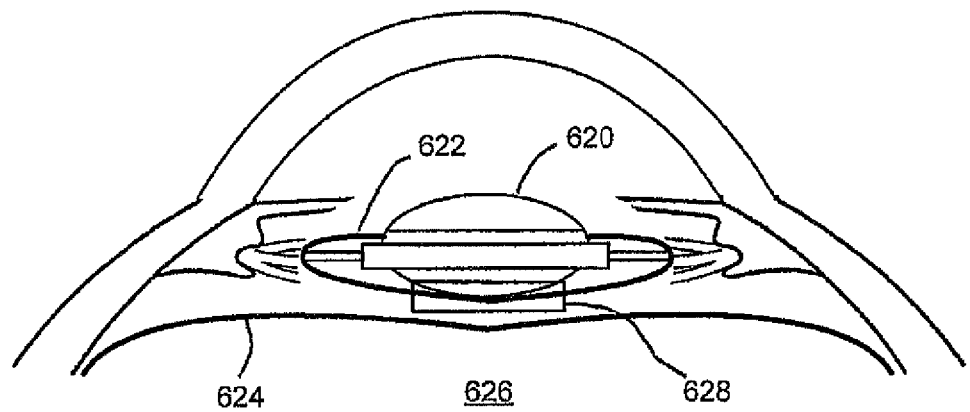
FIG. 40 is a side view diagram showing the adjacent portion of the anterior hyaloids surface of the vitreous displaced relative to the IOL of FIG. 39 and a closed boundary incision surface transecting the lens posterior capsule that can be formed by the laser surgery system of FIG. 1, in accordance with many embodiments.

FIG. 39 illustrates an IOL 620 positioned in a lens capsule 622 and an adjacent portion of the anterior hyaloid surface 624 of the vitreous 626. To avoid damage to the anterior hyaloids surface 624 so as to avoid compromising containment of the vitreous 626, the anterior hyaloid surface 624 can be separated and displaced relative to the posterior portion of the lens capsule 622 using any suitable approach. For example, a suitable fluid can be injected into the eye forward of the anterior hyaloid surface so as to separate the anterior hyaloid surface from the posterior portion of the lens capsule 622. FIG. 40 illustrates the adjacent portion of the anterior hyaloid surface 624 displaced relative to the IOL 624 and a closed boundary incision surface 628 transecting the posterior portion of the lens capsule 622. The closed boundary incision surface 628 can be formed using any suitable system or method, including those described herein such as the laser surgery system 10. For example, the closed boundary incision surface 628 can be formed using concurrent imaging and adaptive tissue treatment as described herein so as to reduce the extent by which the closed boundary incision surface extends on one or both sides of the posterior portion of the lens capsule 622 so as to reduce the probability of damaging the anterior hyaloid surface 624 and/or the IOL 620.

Figure 41:
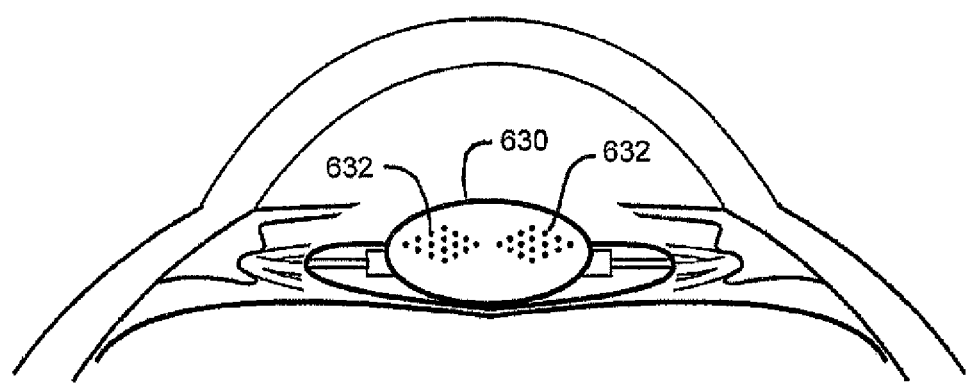
FIG. 41 is a side view diagram showing refractive index changes that can be induced in an IOL by the laser surgery system of FIG. 1, in accordance with many embodiments.

Refractive Correction Via Laser-Induced Modification of Refractive Index of an IOL As described herein, the laser surgery system 10 can be used to modify eye tissue (e.g., corneal tissue) without generating plasma and associated cavitation event. The laser eye surgery system 10 can also be used to modify an IOL in situ without generating plasma and associated cavitation event. FIG. 41 illustrates an IOL 630 that has been modified by using the laser eye surgery system 10 to induce a plurality of small localized modification 632. In many embodiments, the small localized modifications 632 are accomplished so as to change the refractive index of the IOL material within the small localized modifications 632. Such localized modification of refractive index can be used to controllably configure the refractive index profile of the IOL 630 so as to impose a desired refractive correction without removal of the IOL 630 from the patient's eye. Suitable IOL targets include acrylic IOLs or in general all materials that have at least some transmission of the laser wavelength to enable the modification. Other IOL materials are feasible as long as suitable transmission is provided. Modification of the refractive index may be in the order of about 10%, so in the case of acrylic with an index of refraction of 1.4914 it may be modified to have an index of refraction of about 1.6405 or to about 1.3423.

Lens Fragmentation

The laser surgery system 10 can be configured incise a crystalline lens. For example, the electromagnetic radiation beam 28 generated by the laser assembly 12 can have a wavelength that is suitably transmissible by the crystalline lens, such as, for example, a wavelength between 800 nanometers and 1100 nanometers.

Figure 42:
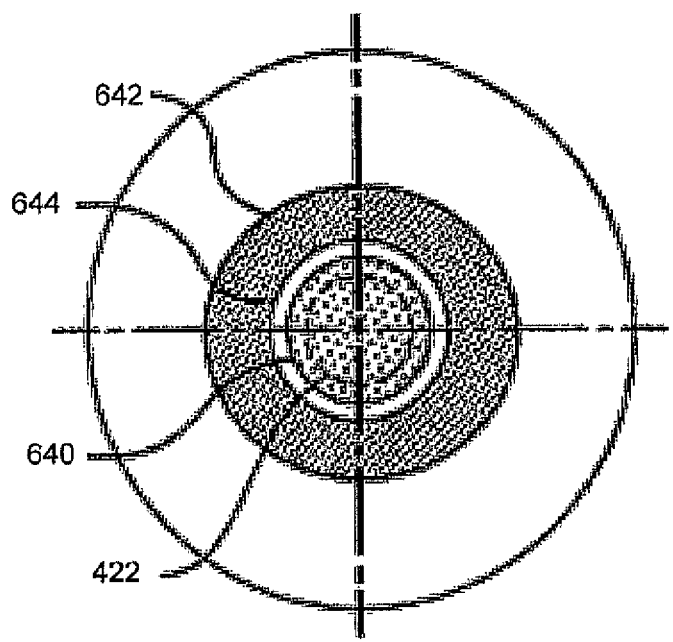
FIGS. 42 through 44 illustrate aspects of lens fragmentation incisions that can be formed by the laser surgery system of FIG. 1, in accordance with many embodiments.

FIG. 42 shows a capsulotomy incision designator 422 and a fragmentation boundary designator 640, in accordance with many embodiments, overlaid on a plan view of an eye that shows the location of the limbus 642 and the pupil 644. In many embodiments, each of the capsulotomy incision designator 422 and the fragmentation boundary designator 640 is positioned and sized to maintain at least a minimum suitable safe working distance from the pupil 644 to avoid having the electromagnetic radiation beam 28 be incident on the pupil 644 to avoid associated damage of the pupil 644. Accordingly, the fragmentation boundary designator 640 can be used in conjunction with the pupil 644 to determine a corresponding iris safety margin distance.

Figure 43:
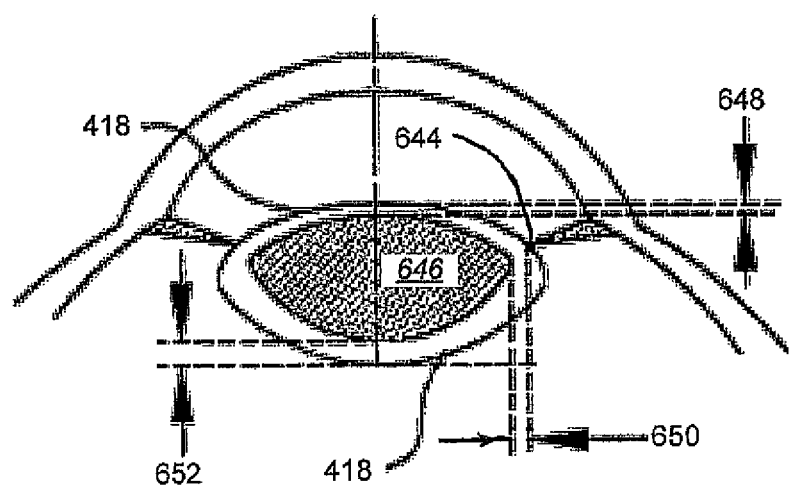

FIG. 43 shows a cross-sectional diagram of an eye that illustrates a lens fragmentation volume 646 defined to maintain an anterior safety margin distance 648 from the anterior portion of the lens capsule 418, an iris safety margin distance 650 from the pupil 644, and a posterior safety margin distance 652 from the posterior portion of the lens capsule 418. As described herein, the laser surgery system 10 can be used to identify the location of a boundary of an intraocular target, and can be configured to identify a suitable set of locations on the anterior and posterior lens capsule. For example, the focal point can be scanned using a low imaging-only power level (e.g., a power level sufficient to locate a suitable set of locations on the anterior and posterior portions of the lens capsule 418 via processing of the signal generated by the detection sensor 54 of the confocal detection assembly 14 without modifying eye tissue) along a suitable path selected to cross the anterior and/or posterior portion of the lens capsule 418 to locate positions on the lens capsule 418 at a sufficient number of locations to support definition of the lens fragmentation volume 646.

Figure 44:
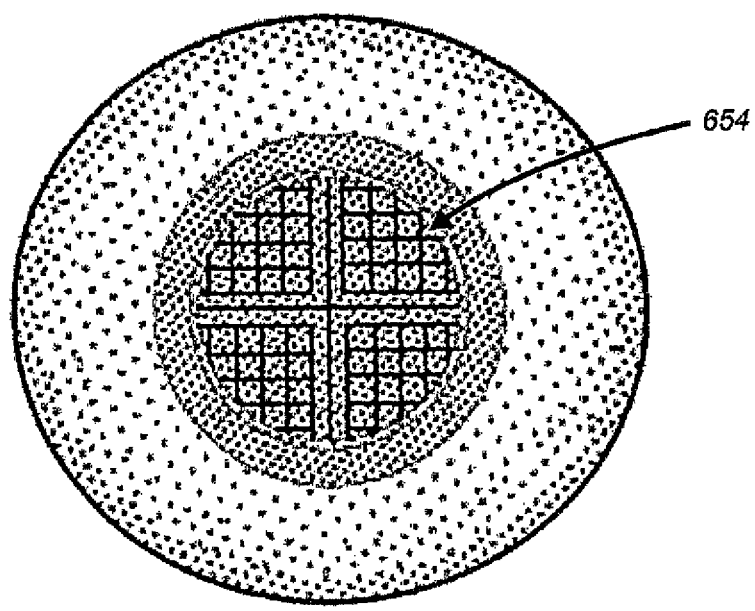
Figure 46:
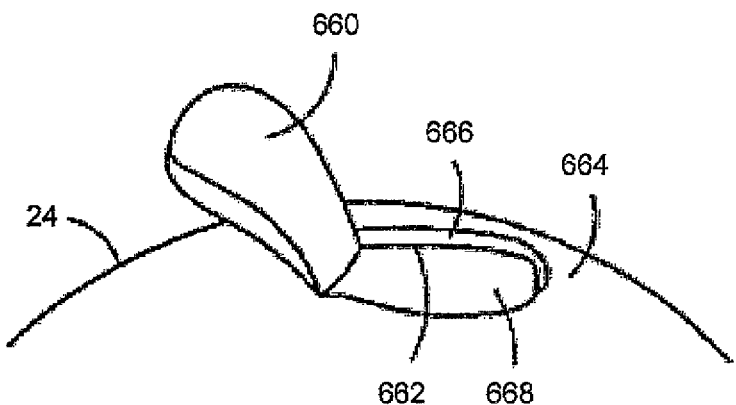
FIG. 46 is a perspective view of a corneal flap that can be formed by the laser surgery system of FIG. 1, in accordance with many embodiments.
Figure 47:
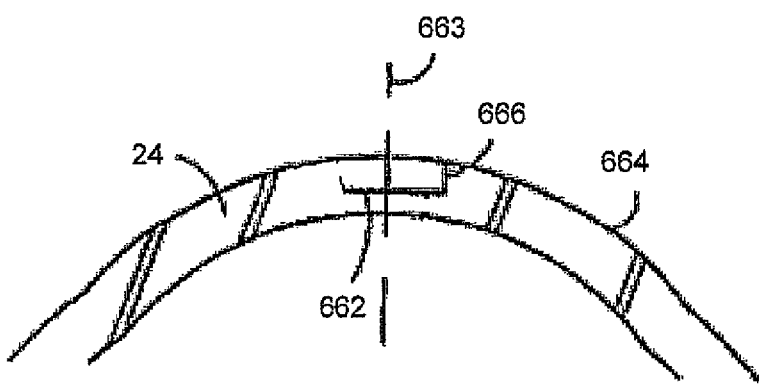
FIG. 47 is a cross-sectional view of a cornea after the periphery and edge of the corneal flap of FIG. 46 have been incised by the laser surgery system of FIG. 1.
Figure 48:
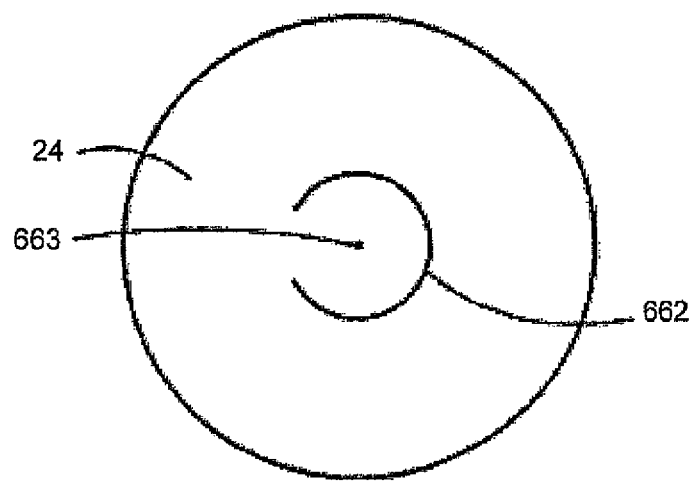
FIG. 48 is a plan view of a cornea after the periphery and edge of the corneal flap of FIG. 46 have been incised by the laser surgery system of FIG. 1.
Figure 49:
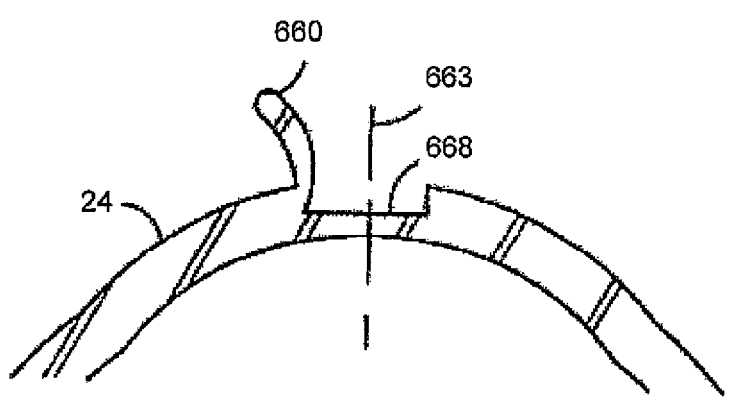
FIG. 49 is a cross-sectional view of a corneal flap of FIG. 46 shown peeled back from the cornea.

Referring now to FIG. 44, in many embodiments, the laser surgery system 10 is configured to create a pattern of intersecting incisions 654 within the lens fragmentation volume 646 so as to fragment the lens within the lens fragmentation volume 646 into discrete fragments configured (e.g., sized, shaped) for subsequent removal from the lens capsule 418. While any suitable lens fragmentation parameters can be employed, example lens fragmentation parameters, including fragmentation patterns, cut dimensions for lens segmentation and softening, laser settings, and applicable safety margins, are illustrated in FIG. 45 and provided in Tables 1 and 2.

TABLE 1

User-adjustable Lens Fragmentation Parameters

| Feature | Default | Range | Step Size | Units |
| --- | --- | --- | --- | --- |
| Diameter | * | 3.0-10.0 | 0.5 | mm |
| Horizontal Spot Spacing | 10 | 5-25 | 2.5 | µm |
| Vertical Spot Spacing | 40 | 10-100 | 10 | µm |
| Pulse Energy, Anterior** | 8 | 1-10 | 0.5 | µJ |
| Pulse Energy, Posterior** | 10 | 1-10 | 0.5 | µJ |
| Seg-Soft Spacing | 500 | 100-1500 | 100 | µm |
| Grid Spacing | 500 | 100-2000 | 100 | µm |

* Default diameter is defined by available pupil diameter - 2*safety margin.
**Pulse energy to vary stepwise (linear) from posterior to anterior, if different

TABLE 2

Lens Fragmentation Safety Margins

| Feature | Default | Range | Step Size | Units |
| --- | --- | --- | --- | --- |
| Iris | 500 | N/A | N/A | µm |
| Anterior *** | 500 | 200-1000 | 100 | µm |
| Posterior *** | 500 | 500-1000 | 100 | µm |

*** Safety margins follow lens surface contours.

Corneal Flaps

In many embodiments, the laser surgery system 10 is configured to incise corneal flaps. Referring now to FIG. 46 through FIG. 49, a corneal flap 660 prepared in accordance with many embodiments is shown. The flap 660 can be prepared in any suitable sequence. For example, the flap 600 can be prepared by first using the laser surgery system 10 to laser incise a posterior surface 662 for the flap 660. The posterior surface 662 can have any suitable configuration. For example, the posterior surface 662 can have a perimeter that is a curved line centered approximately on the optical axis 663 of the eye 24 and extending through an arc of about two hundred and seventy degrees. With the posterior surface 662 established, the laser surgery system 10 can be used to form an incision extending from the anterior surface 664 of the cornea 24 to the perimeter of the posterior surface 662 to establish an edge 666 for the flap 660. Once the edge 666 is incised, the flap 30 can be raised to expose a bed of stromal tissue 668. After exposure, the bed of stromal tissue 668 can be, for example, photoablated using an excimer laser (not shown). After photoablation with the excimer laser, the flap 660 can be repositioned over the bed of stromal tissue 668 and allowed to heal. The result is a reshaped cornea 24.

Intra-Stromal Corneal Incisions

Figure 50:
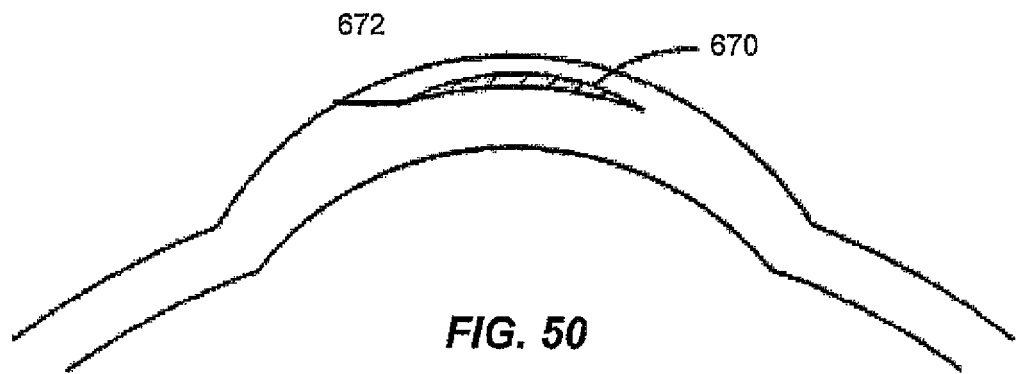
FIG. 50 and FIG. 51 are cross-sectional views of a cornea illustrating example intra-stromal incised volumes, in accordance with many embodiments, that can be created by the laser surgery system of FIG. 1.
Figure 51:
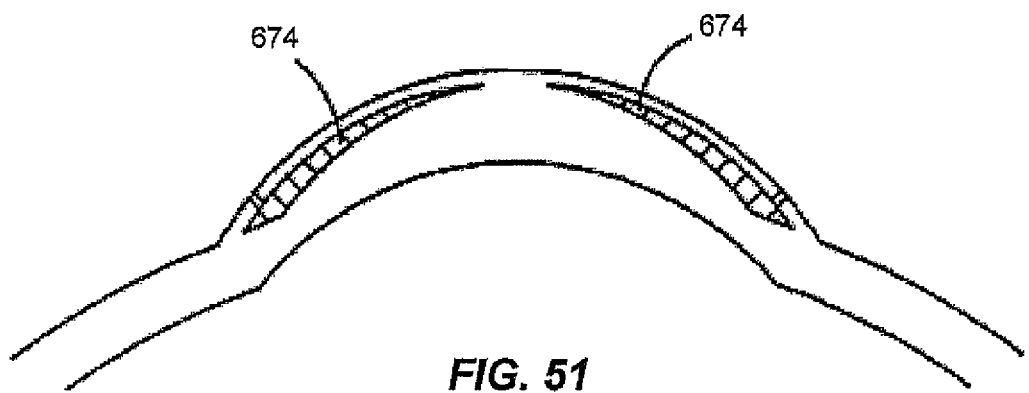

In many embodiments, the laser surgery system 10 is configured to create intra-stromal corneal incisions that can, for example, be used to correct refractive errors. For example, FIG. 50 is a cross-sectional view of a cornea illustrating an incised volume 670 that is separated from surrounding intra-stromal tissue of the cornea by enclosing incision surfaces created by the laser surgery system 10. The illustrated incised volume 670 is axially-symmetric about the optical axis of the eye. The laser surgery system 10 can be used to form an access incision 672 of suitable configuration to allow removal of the incised volume 670. Removal of the incised volume 670 results in reshaping of the cornea so as to modify the refractive properties of the cornea. One or more incised volumes of any suitable configuration can be incised and removed to reshape the cornea so as to modify the refractive properties of the cornea. For example, the incised volume 670 illustrated in FIG. 50 is configured to modify the refractive properties of the cornea to correct myopia. As another example, FIG. 51 illustrates an annularly-shaped incised volume 674 that can be laser incised by the laser surgery system 10 and then removed to reshape the cornea to correct hyperopia. The illustrated incised volume 674 is axially-symmetric about the optical axis of the eye. One or more additional incisions can be laser formed by the laser surgery system 10 to divide the incised volume 670, 674 into suitably sized portions to facilitate their removal. While the illustrated incised volumes 670, 674 are both axially-symmetric and configured to correct myopia and hyperopia, respectively, any other suitably configured incised volume(s) can be incised so as to effect a desired reshaping of the cornea corresponding to a desired refractive modification of the cornea.

Corneal Inlay Pockets

Figure 52:
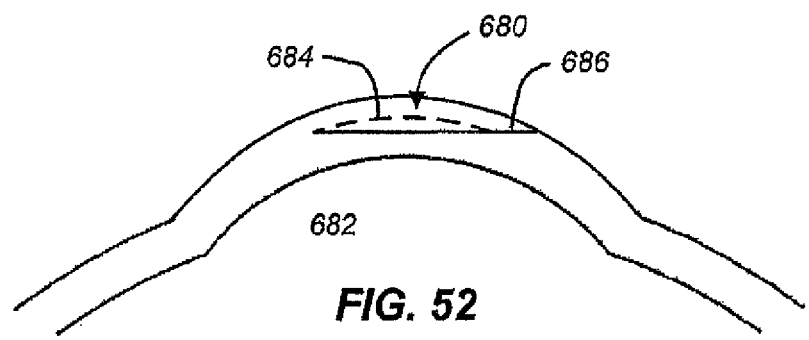
FIG. 52 and FIG. 53 are a cross-sectional view and a plan view of a cornea, respectively, and illustrate a corneal intra-stromal pocket, in accordance with many embodiments, that can be created by the laser surgery system of FIG. 1.
Figure 53:
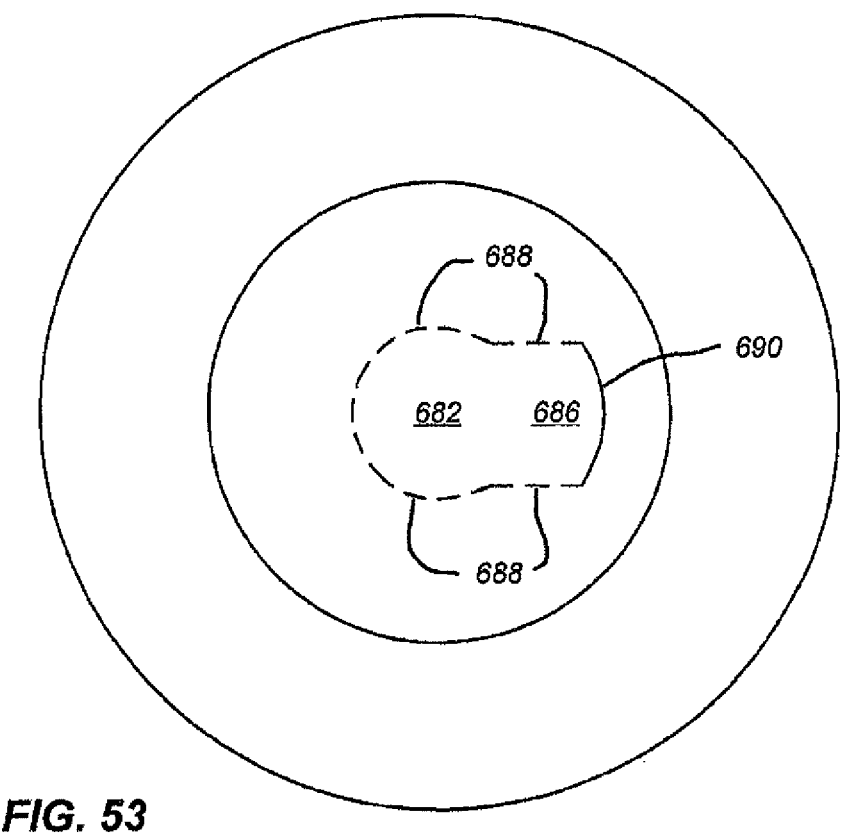

Referring now to FIG. 52 and FIG. 53, which show a cross-sectional view and a plan view of a cornea, respectively, the laser surgery system 10 can be configured to create an intra-stromal pocket 680 in a cornea. The intra-stromal pocket 680 is configured to accommodate an inserted intra-stromal inlay. The intra-stromal pocket 680 is defined by one or more intra-stromal incision surfaces 682, 684 that are laser incised by the laser surgery system 10. For example, the intra-stromal pocket 680 can be defined by a single incision surface 682 (e.g., a circular planar intrastromal incision) configured to accommodate and position an inserted intra-stromal inlay. The intra-stromal pocket 680 can also be defined by incising a volume and removing the incised volume to leave a three-dimensional intra-stromal pocket configured to accommodate and position an inserted intra-stromal inlay. For example, the intra-stromal pocket 680 can be defined by incising a volume bounded by the illustrated incision surfaces 682, 684, both of which are axially-symmetrically shaped relative to the visual axis of the eye. The laser surgery system 10 can be used to create an access incision 686 that extends from the intra-stromal pocket 680 insertion to the anterior surface of the cornea. The combination of the intra-stromal pocket 680 and the access incision 686 has an intra-stromal perimeter 688 and an exposed perimeter 690 disposed on the anterior surface of the cornea. An intra-stromal inlay can then be inserted into the intra-stromal pocket 680 through the access incision 686 without the creation of a full corneal flap.

The intra-stromal pocket 680 can be formed so as to accommodate and position and/or orient any suitable intra-stromal inlay. For example, the intra-stromal pocket 680 can have a circular perimeter and be configured to accommodate and position a correspondingly sized circular disk-shaped intra-stromal inlay. As another example, the intra-stromal pocket 680 can have a non-circular perimeter of any suitable shape (e.g., ellipse, rectangular, polygonal) and be configured to accommodate, position, and orient a correspondingly sized and shaped intra-stromal inlay, thereby controlling the angular orientation of the inserted intra-stromal inlay relative to the optical axis of the eye. Such control of angular orientation of the inserted intra-stromal inlay can be used to, for example, treat astigmatism. An example of an intra-stromal inlay for which the laser assembly 10 can create a corresponding intra-stromal pocket 680 includes an opaque circular micro-disc with a small opening in the center, for example, the KAMRA™ inlay.

DSEK/DMEK/DALK and PK Incisions

The laser surgery system 10 can be configured to create corneal surgical incisions such as Descemet's Stripping Endothelial Keratoplasty (DSEK), Descemet's Membrane Endothelial Keratoplasty (DMEK), Deep Anterior Lamellar Keratoplasty (DALK), and/or Penetrating Keratoplastic (PK). DSEK, DMEK, DALK, and PK corneal incisions are used to treat corneal diseases in which one or more portions of the cornea are dysfunctional and are surgically removed and exchanged. Because the laser surgery system 10 is operable to form precise corneal incisions, better clinical results and better patient satisfaction may result with regard to DSEK, DMEK, DALK, and/or PK corneal incisions as compared to less precise approaches.

Enhanced Patient Clearance

Figure 54:
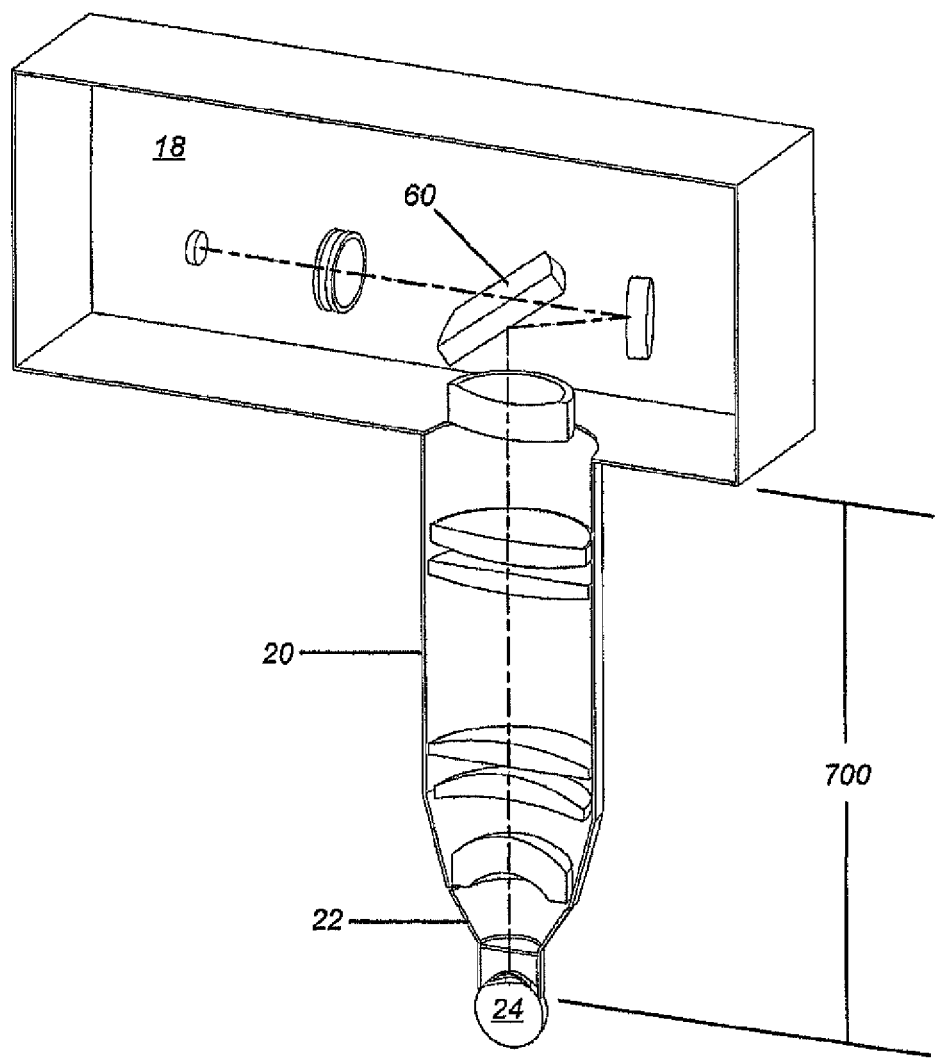
FIG. 54 illustrates a configuration of a scanning assembly and an objective lens assembly, in accordance with many embodiments of the laser surgery system of FIG. 1, that are configured to provide substantial clearance between the scanning assembly and the patient without using a lens relay and with a reduced diameter objective lens assembly.

Referring now to FIG. 54, in many embodiments of the laser surgery system 10, the scanning assembly 18 and the objective lens assembly 20 are configured to provide a clearance 700 (e.g., between 100 and 250 millimeters in many embodiments with the illustrated clearance being approximately 175 millimeters) between the scanning assembly 18 and the patient 24 without using a lens relay. The clearance 700 is achieved by utilizing an optical design that is constrained by target physical size parameters while being configured to create precise incisions within a desired scan volume without using a lens relay. The clearance 700 is desirable for both the physician and the patient. For the physician, adequate clearance enhances visibility of the patient during the patient docking process, and provides room for the physician to grasp the objective lens assembly 20 directly for easy manipulation of the position of the objective lens assembly 20 relative to the patient. For the patient, the clearance 700 may help reduce the possibility of excessive patient movement that may arise due to patient anxiety stemming from a claustrophobic reaction to the proximity of the scanning assembly 18.

Figure 55:
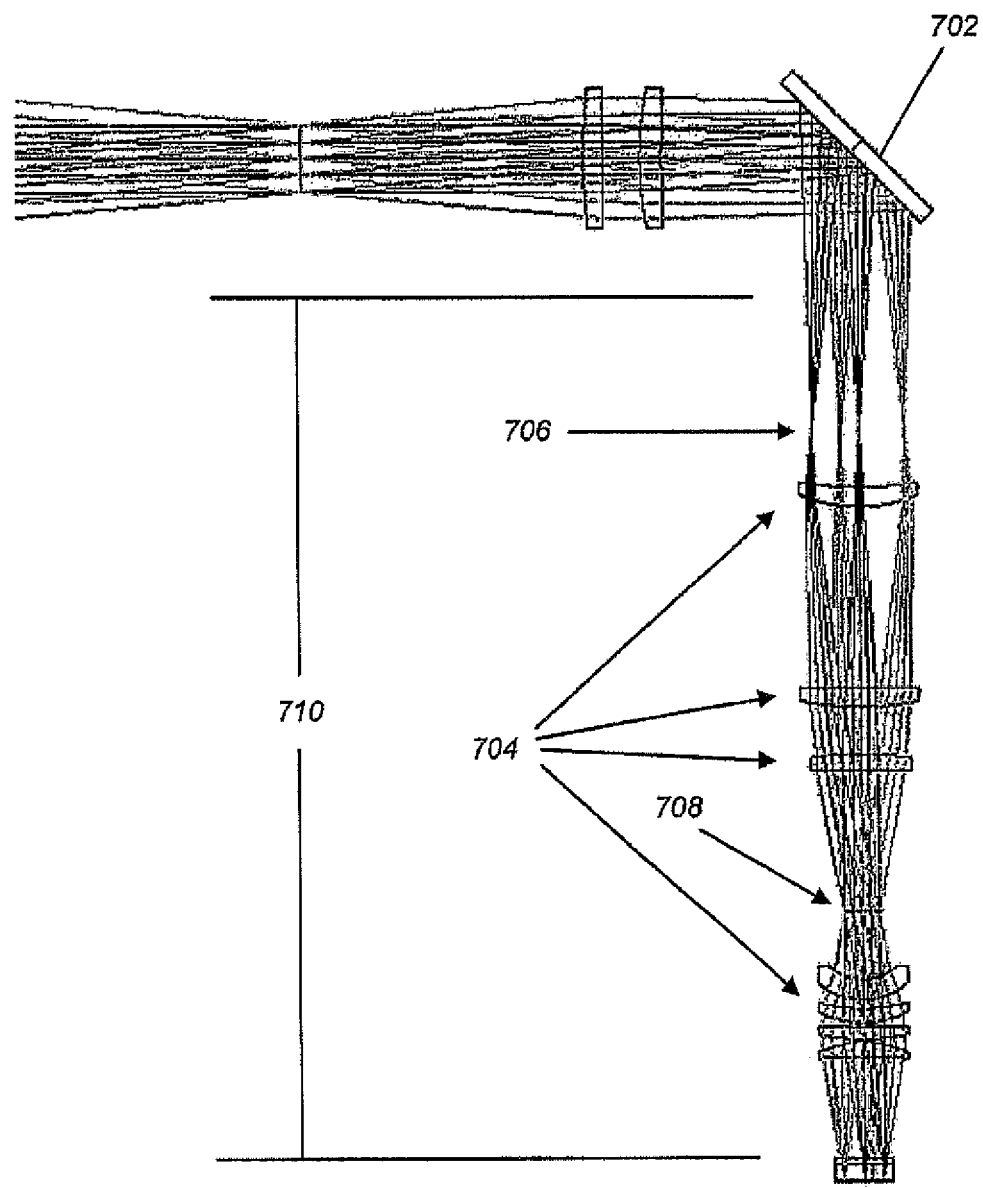
FIG. 55 illustrates an objective lens assembly that utilizes a lens relay and associated excessive clearance between the scanning assembly and the patient.

Significant design parameters relative to the configuration of the scanning assembly 18 and the objective lens assembly 20 include the desired scan volume (e.g., desired cut radius at each of various depths within the patient's eye), the strehl ratio (laser focused spot quality), telecentricity, desired patient clearance, number of optical elements (lenses), and not utilizing a lens relay. By balancing these parameters, a patient clearance of approximately 175 millimeters and objective lens housing of approximately 60 millimeters in diameter were achieved. An important aspect to achieving an efficient configuration for objective lens assembly 20 without the use of a lens relay is the use of a small number of high optical power negative and positive lenses. In the illustrated embodiment, the objective lens assembly 20 does not utilize a lens relay, which would require a larger number of lenses and create a patient clearance far in excess of that required to provide adequate access for the physician and of that required to adequately reduce patient discomfort due to a claustrophobic reaction to the proximity of the instrument. In contrast, FIG. 55 illustrates an objective lens assembly 704 that utilizes a lens relay (as evidenced by beam crossover locations 706, 708) and has a clearance 710 of approximately 340 mm, which exceeds the clearance 700 of between 100 and 250 mm and is thus significantly beyond a presently preferred range of clearances for this application.

In many embodiments, the scanning assembly 18 is also configured to minimize the diameter of the objective lens housing. For example, in many embodiments, the scanning assembly 18 includes an xy-scan device 60, which is operable to deflect the beam 28 in two dimensions transverse to the direction of propagation of the beam 28. In many embodiments, the xy-scan device 60 includes a single deflectable mirror that is controllably deflectable to scan the beam 28 in two dimensions transverse to the direction of propagation of the beam 28. By using a single mirror as opposed to two or more mirrors, the diameter of the objective lens housing can be reduced due to the ability to avoid additional transverse displacement of the beam 28 associated with the use of two or more scanning mirrors.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for laser eye surgery while accommodating patient movement, the method comprising:
   generating a first electromagnetic radiation beam by a beam source;
   propagating the first electromagnetic radiation beam from the beam source to an xy-scanning mirror along a variable optical path;
   changing an optical path length of the variable optical path between the beam source and a pivot point of the xy-scanning mirror by freely floating the pivot point of the xy-scanning mirror in tandem with movement of the eye in a z-dimension;
   focusing the first electromagnetic radiation beam to a first focal point at a location within the eye;
   scanning the first focal point to different locations within the eye in at least one dimension transverse to a propagation direction of the first electromagnetic radiation beam by the xy-scanning mirror;
   wherein the changing the optical path length accommodates the movement of the eye and corresponding movement of the pivot point of the xy-scanning mirror relative to the beam source while maintaining alignment between the eye and the scanned electromagnetic radiation beam;
   propagating a portion of the first electromagnetic radiation beam reflected from the focal point location back along a portion of the variable optical path to a sensor;
   generating an intensity signal by the sensor, the intensity signal being indicative of the intensity of the portion of the first electromagnetic radiation beam reflected from the first focal point location and propagated to the sensor;
   generating a second electromagnetic radiation beam configured to modify eye tissue;
   propagating the second electromagnetic beam to the xy-scanning mirror along the variable optical path;
   focusing the second electromagnetic radiation beam to a second focal point; and
   scanning the second focal point within the eye by the xy-scanning mirror to create a corneal incision in the eye.

2. The method of claim 1, wherein the corneal incision is an intra-stromal corneal incision.

3. The method of claim 2, wherein an incised volume of the intra-stromal corneal incision is axially symmetric about the optical axis of the eye.

4. The method of claim 3, wherein the incised volume is configured to reshape the cornea so as to modify one or more refractive properties of the cornea.

5. The method claim 3, wherein the corneal incision further comprises an access incision configured to allow removal of the incised volume.

6. The method of claim 5, further comprising removing the incised volume.

7. The method of claim 1, further comprising supporting the xy-scanning mirror by a first support assembly so as to accommodate relative movement between the xy-scanning mirror and the first support assembly so as to accommodate the movement of the eye.

8. The method of claim 7, further comprising:
   supporting the first support assembly by a second support assembly so as to accommodate relative movement between the first support assembly and the second support assembly so as to accommodate the movement of the eye; and
   supporting a first reflector by the first support assembly, the first reflector being configured to reflect the electromagnetic radiation beam so as to propagate to the xy scanning mirror along a portion of the variable optical path.

9. The method of claim 8, further comprising:
   supporting the second support assembly by a base assembly so as to accommodate relative movement between the second support assembly and the base assembly so as to accommodate the movement of the eye; and
   supporting a second reflector by the second support assembly, the second reflector being configured to reflect the electromagnetic radiation beam to propagate along a portion of the variable optical path so as to be incident on the first reflector.

10. The method of claim 1, wherein generating the intensity signal comprises passing a reflected portion of the first electromagnetic radiation beam through an aperture to block portions of the first electromagnetic radiation beam reflected from locations other than the first focal point location.

11. The method of claim 1, further comprising:
   passing the first electromagnetic radiation beam through a polarization-sensitive device;
   modifying polarization of at least one of the first electromagnetic radiation beam and a portion of the first electromagnetic radiation beam reflected from the focal point location; and
   reflecting a portion of the first electromagnetic radiation beam reflected from the first focal point location by the polarization-sensitive device so as to be incident upon the sensor.

12. The method of claim 1, wherein the first electromagnetic radiation beam is not configured to modify tissue.

13. The method of claim 1, wherein the first electromagnetic radiation beam and the second electromagnetic beam are the same electromagnetic beam.

14. The method of claim 1, wherein the second electromagnetic radiation beam comprises a plurality of laser pulses having a wavelength between 320 nanometers and 430 nanometers.

15. The method of claim 1, wherein the second electromagnetic radiation beam comprises a plurality of laser pulses having a wavelength between 800 nanometers and 1100 nanometers.

* * * * *